(12) United States Patent
Kim

(10) Patent No.: US 10,575,972 B2
(45) Date of Patent: Mar. 3, 2020

(54) MEDICAL DEVICE WITH INDUCTION TRIGGERED ANCHORS AND SYSTEM FOR DEPLOYMENT OF THE SAME

(71) Applicant: Cook Medical Technologies LLC, Bloomington, IN (US)

(72) Inventor: Woong Kim, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 92 days.

(21) Appl. No.: 15/581,980

(22) Filed: Apr. 28, 2017

(65) Prior Publication Data
US 2018/0311055 A1 Nov. 1, 2018

(51) Int. Cl.
*A61F 2/82* (2013.01)
*A61F 2/848* (2013.01)
(Continued)

(52) U.S. Cl.
CPC ................ *A61F 2/848* (2013.01); *A61F 2/07* (2013.01); *A61F 2/966* (2013.01); *A61F 2/958* (2013.01); *A61F 2002/8483* (2013.01); *A61F 2002/8486* (2013.01); *A61F 2002/9517* (2013.01); *A61F 2002/9583* (2013.01);
(Continued)

(58) Field of Classification Search
CPC ...... A61F 2002/9517; A61F 2002/8486; A61F 2002/8483; A61F 2002/9583; A61F 2210/0014; A61F 2210/0038; A61F 2/958; A61F 2/966; A61F 2/07; A61F 2/848; A61B 17/11; A61B 17/1114; A61B 2017/1107; A61B 2017/1121; A61B 2017/111; A61B 2017/1132;
(Continued)

(56) References Cited

U.S. PATENT DOCUMENTS 5,025,799 A 6/1991 Wilson
5,820,595 A 10/1998 Parodi
(Continued)

FOREIGN PATENT DOCUMENTS

AU 2011204895 A1 8/2011

OTHER PUBLICATIONS

European search report/opinion for corresponding application No. 18275059.6 dated Sep. 25, 2018.
(Continued)

*Primary Examiner* — Erich G Herbermann
(74) *Attorney, Agent, or Firm* — Brinks Gilson & Lione

(57) ABSTRACT

A medical device, deployment systems and methods of use thereof are provided. The medical device includes at least one anchor element coupled to a device body. The anchor element has a first configuration disposed about an anchor axis and configured to pierce a body tissue wall. In a second configuration, the anchor elements have an enlarged shape, and in response to a temperature rise in the anchor element, the pierced body tissue wall is drawn closer to the device body. The anchor element maintains alignment substantially with the anchor axis to inhibit tearing of the pierced body tissue wall by the anchor element. The system may include balloons for targeting the radial pressure of the anchor elements into the body vessel wall. The anchor elements may be made of shape memory materials capable of localized heating due to an induction device.

18 Claims, 14 Drawing Sheets

(51) Int. Cl.
    *A61F 2/966*     (2013.01)
    *A61F 2/07*     (2013.01)
    *A61F 2/95*     (2013.01)
    *A61F 2/958*     (2013.01)

(52) U.S. Cl.
    CPC ............. *A61F 2002/9665* (2013.01); *A61F 2210/0014* (2013.01); *A61F 2210/0038* (2013.01)

(58) Field of Classification Search
    CPC .... A61B 2017/1135; A61B 2017/1139; A61B 2017/1103
    See application file for complete search history.

(56) References Cited

U.S. PATENT DOCUMENTS

| | | | |
|---|---|---|---|
| 5,968,053 | A | 10/1999 | Revelas |
| 6,068,611 | A | 5/2000 | Loffler et al. |
| 6,080,160 | A | 6/2000 | Chen et al. |
| 6,206,888 | B1 | 3/2001 | Bicek et al. |
| 6,238,421 | B1 | 5/2001 | Günther et al. |
| 6,850,804 | B2 | 2/2005 | Eggers et al. |
| 8,366,706 | B2 | 2/2013 | Buchbinder et al. |
| 8,382,834 | B2 | 2/2013 | Prescott |
| 8,840,663 | B2 | 9/2014 | Salahieh et al. |
| 8,876,883 | B2 | 11/2014 | Rust |
| 9,220,906 | B2 | 12/2015 | Griswold et al. |
| 9,307,995 | B2 | 4/2016 | Paul et al. |
| 9,468,517 | B2 | 10/2016 | Shalev |
| 2001/0029396 | A1 | 10/2001 | Wilson et al. |
| 2002/0099437 | A1 | 7/2002 | Anson et al. |
| 2005/0038506 | A1 | 2/2005 | Webler et al. |
| 2005/0267561 | A1* | 12/2005 | Jones ................. A61F 2/958 623/1.11 |
| 2006/0074484 | A1 | 4/2006 | Huber |
| 2006/0252983 | A1 | 11/2006 | Lembo et al. |
| 2007/0073380 | A1 | 3/2007 | Vazquez et al. |
| 2007/0156205 | A1 | 7/2007 | Larson et al. |
| 2008/0071178 | A1 | 3/2008 | Greenland et al. |
| 2008/0103443 | A1 | 5/2008 | Kabrick et al. |
| 2009/0270742 | A1 | 10/2009 | Wolinsky et al. |
| 2010/0249888 | A1 | 9/2010 | Glenn et al. |
| 2011/0172760 | A1* | 7/2011 | Anderson ......... A61B 17/0057 623/1.15 |
| 2011/0262684 | A1 | 10/2011 | Wintsch et al. |
| 2012/0172892 | A1 | 7/2012 | Grubac et al. |
| 2012/0191174 | A1* | 7/2012 | Vinluan ................. A61F 2/07 623/1.12 |
| 2013/0211534 | A1 | 8/2013 | Taylor |
| 2014/0046347 | A1 | 2/2014 | Cully et al. |
| 2014/0207109 | A1 | 7/2014 | Laramy et al. |
| 2015/0257882 | A1 | 9/2015 | Börtlein et al. |
| 2015/0369223 | A1 | 12/2015 | Hallila et al. |
| 2016/0157858 | A1 | 6/2016 | Horton et al. |
| 2016/0331534 | A1 | 11/2016 | Buchbinder et al. |

OTHER PUBLICATIONS

Mark H. Wholey, MD, et al., "Designing the Ideal Stent", Endovascular Today, Mar. 2007, pp. 25-34.
Christian W. Müller et al., "Electromagnetic Induction Heating of an Orthopaedic Nickel—Titanium Shape Memory Device", Journal of Orthopaedic Rsearch Dec. 2010, pp. 1671-1676.
Ronny Pfeifer, et al. "Adaptable Orthopedic Shape Memory Implants", SciVerse ScienceDirect, Procedia CIRP 5 (2013), pp. 253-258.

* cited by examiner

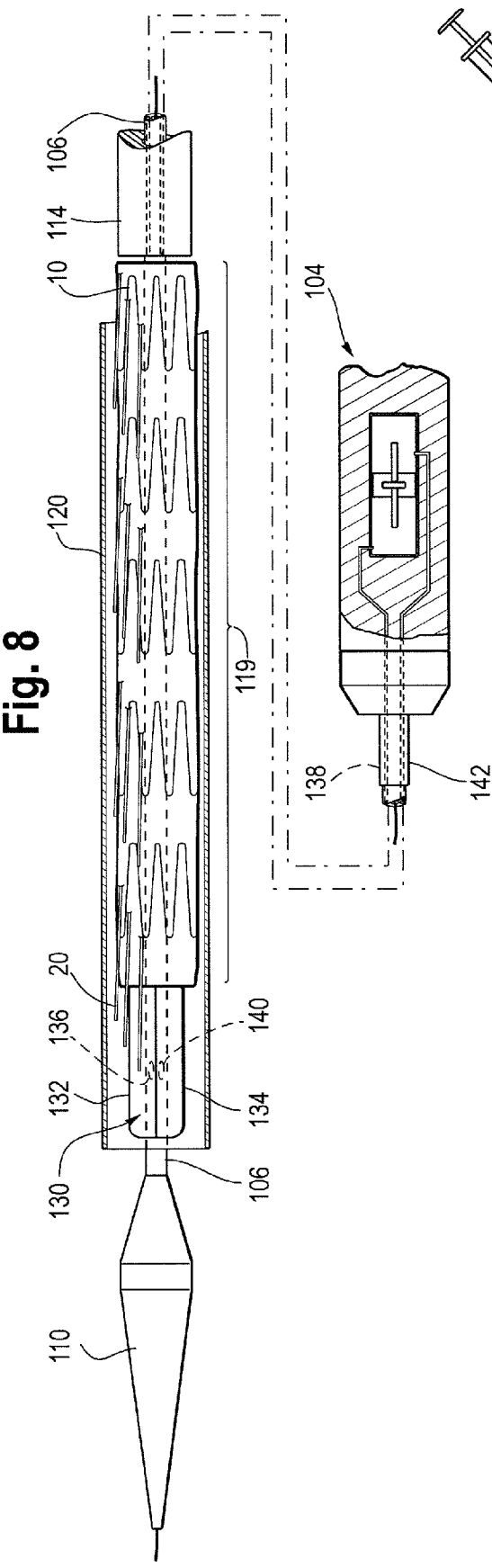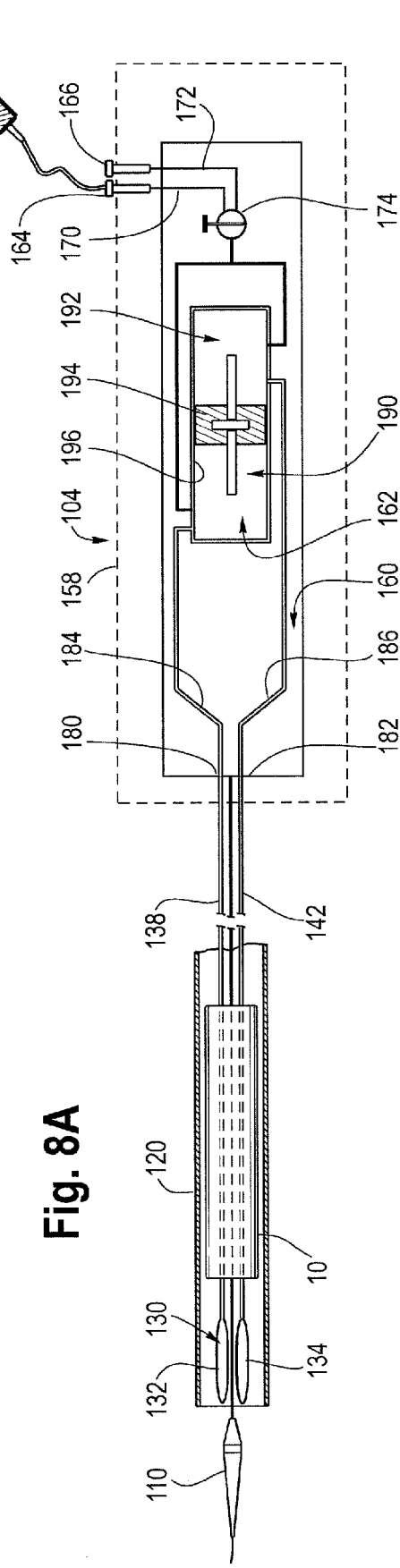

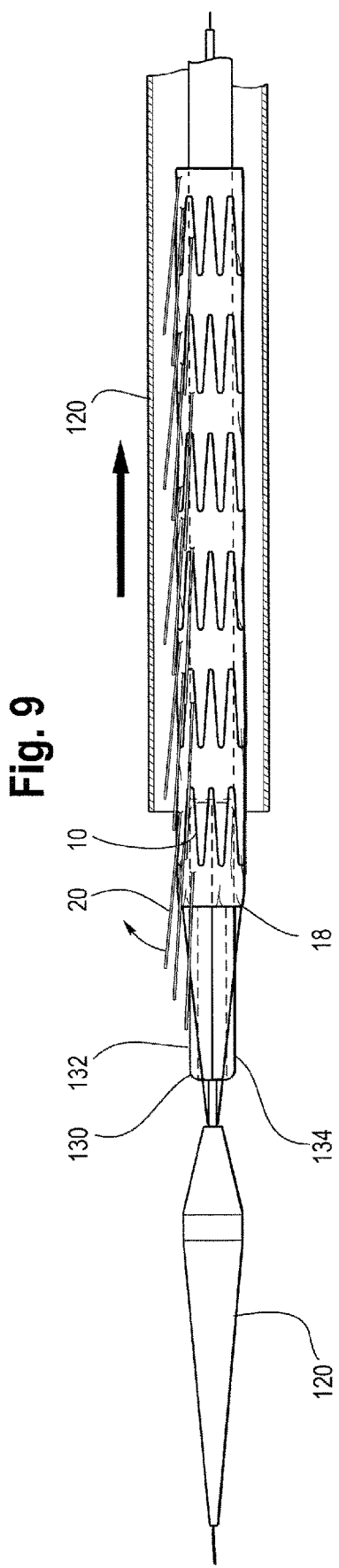

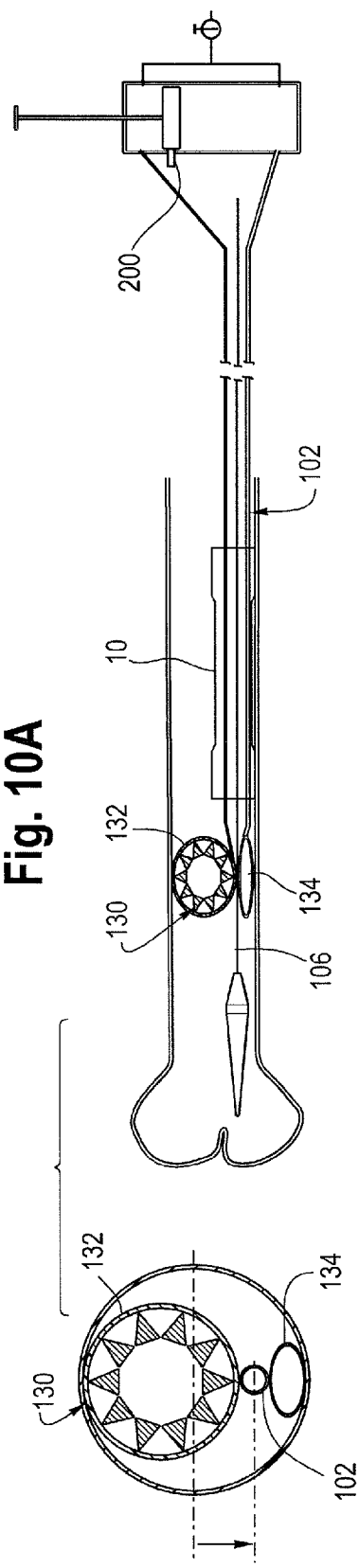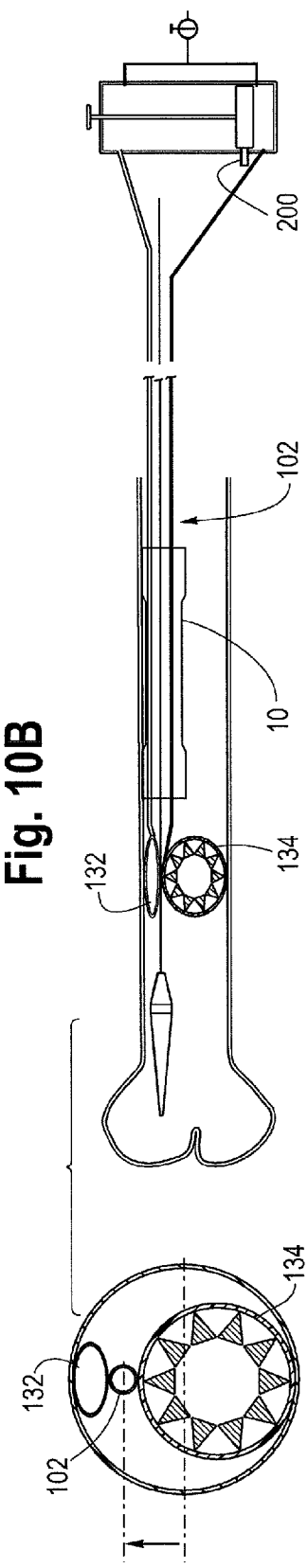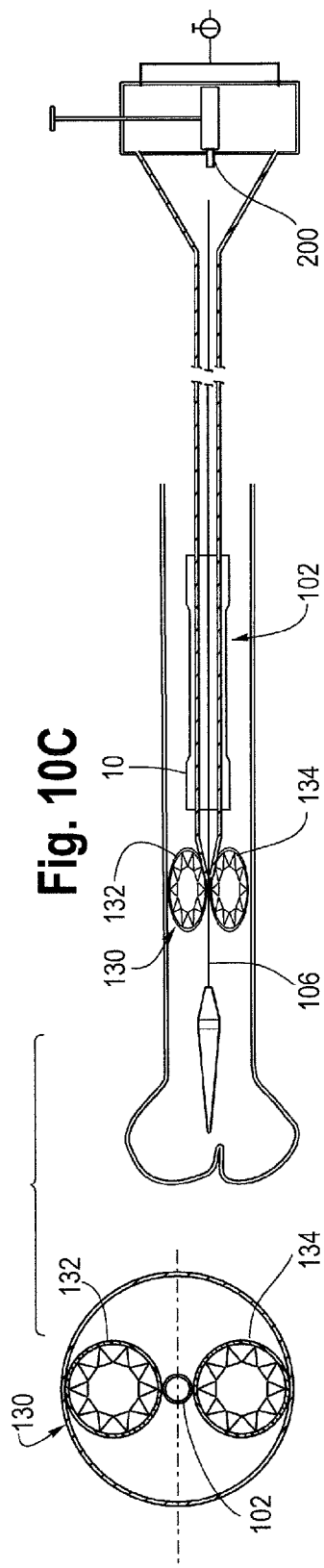

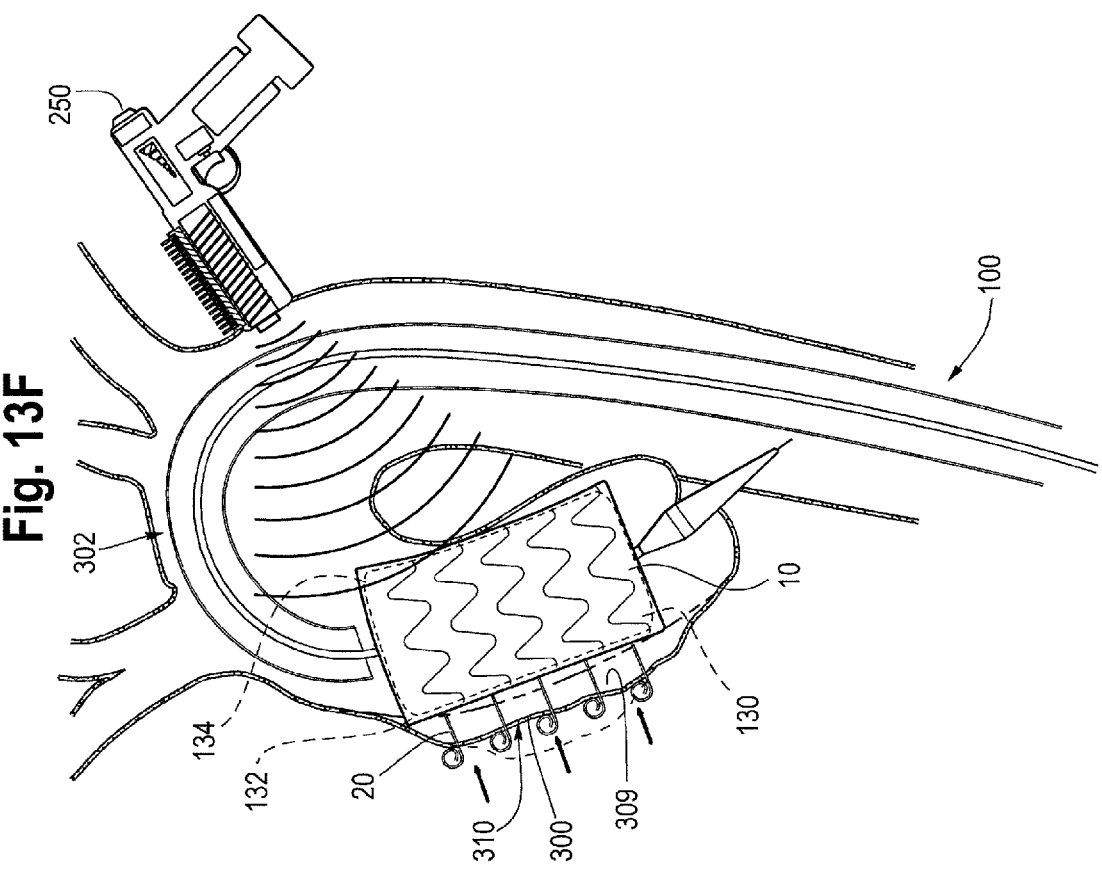
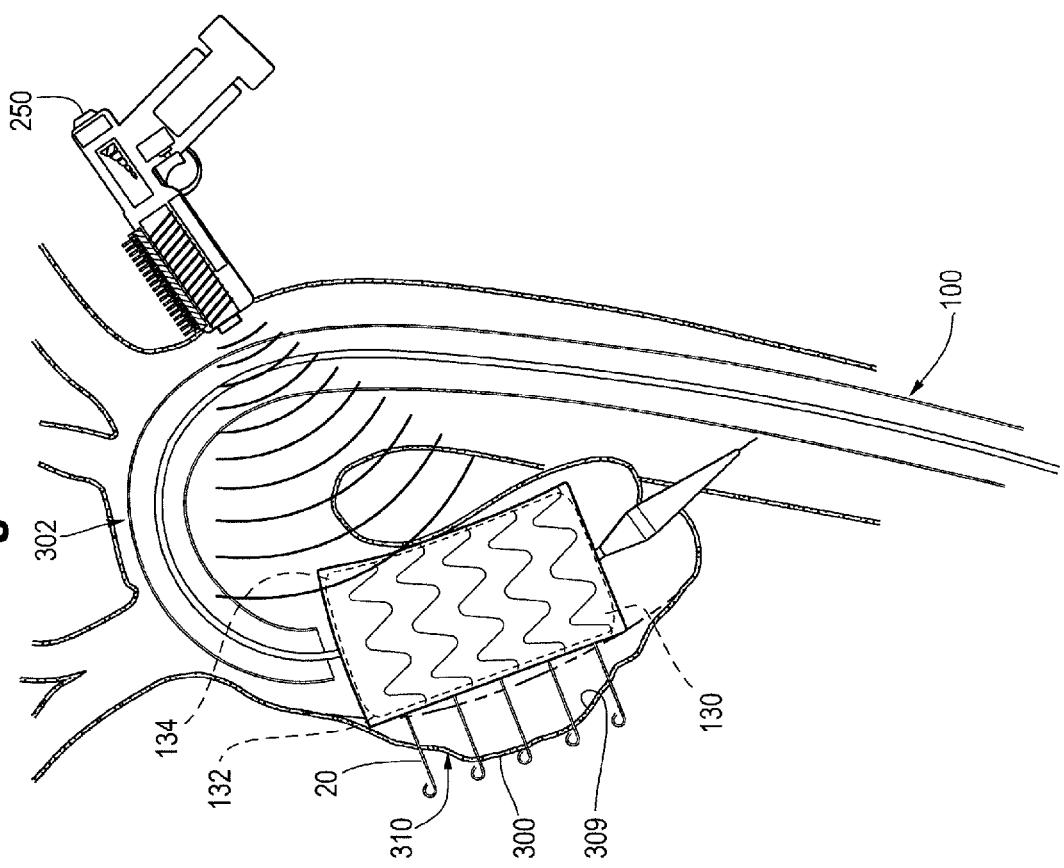

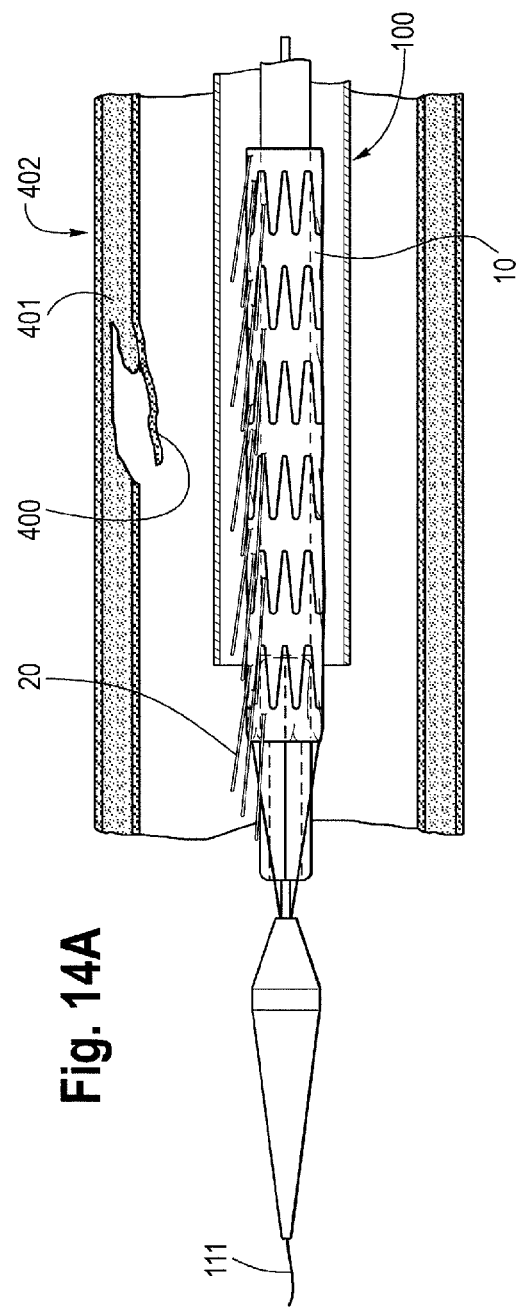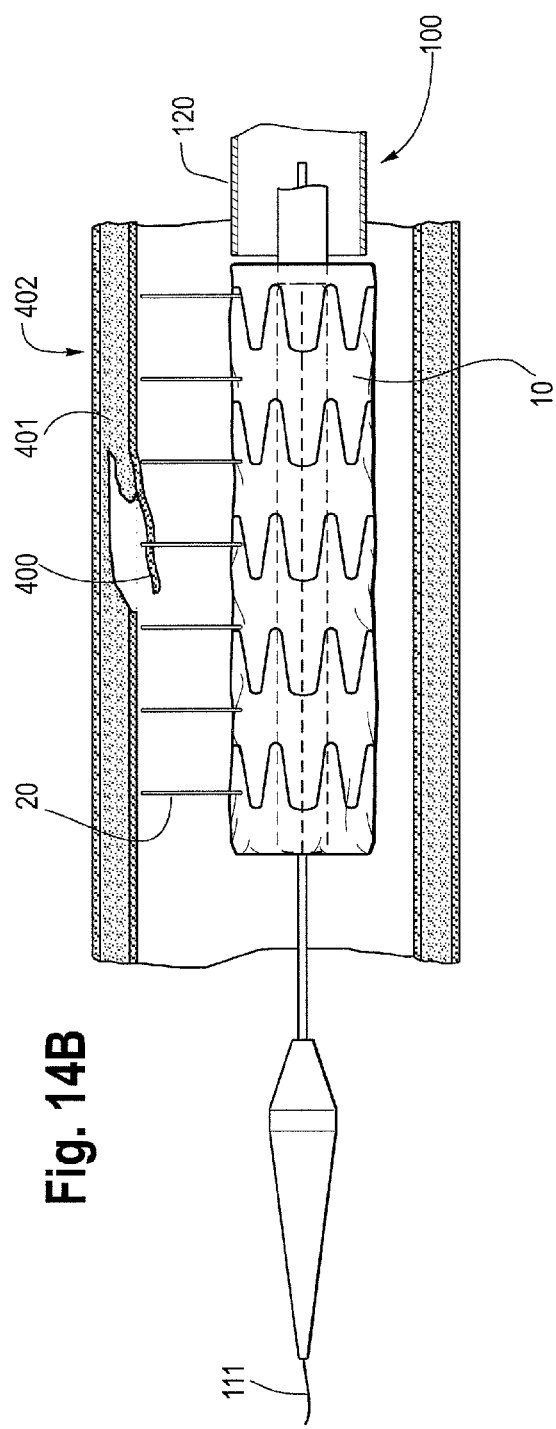

MEDICAL DEVICE WITH INDUCTION TRIGGERED ANCHORS AND SYSTEM FOR DEPLOYMENT OF THE SAME

BACKGROUND

The present disclosure relates generally to medical devices, and particularly, to endoluminal prostheses with induction triggered anchors and systems for deploying such prostheses and methods for the manufacture and use of the same for repair of damaged vessels, ducts, or other physiological pathways.

Various interventions have been provided for weakened, aneurysmal, dissected or ruptured vessels, including surgical interventions and endovascular interventions. Endovascular interventions generally include inserting an endoluminal device or prosthesis such as a stent or stent graft into the damaged or diseased body lumen to provide support for the lumen, and to exclude damaged portions thereof. Such prosthetic devices are typically positioned at the point of treatment or target site by navigation through the vessel, and possibly other connected branch vessels, until the point of treatment is reached. This navigation may require the device to be able to move axially through the vessel(s) prior to deployment, while still maintaining the ability to exert an outward force on the interior wall once deployed.

In the field of aortic interventions, endoluminal devices are placed in vessels to address and correct diseased tissue resulting from atherosclerotic plaques, aneurysm or weakening of body vessel walls, and arterial dissection. In the case of atherosclerosis, plaque buildup results in narrowing of the vessel which may lead to reduced or blocked blood flow within the body vessel. Endoluminal device for atherosclerosis acts to radially expand the narrowed area of the body vessel to restore normal blood flow. In the case of an aneurysm, a weakening of the body vessel wall results in ballooning of the body vessel which can eventually lead to rupture and subsequent blood loss. In some cases, the aneurysmal sac may include plaque. Endoluminal device for aneurysms acts to seal off the weakened area of the body vessel to reduce the likelihood of the body vessel rupture. In the case of arterial dissection, a section of the innermost layer of the arterial wall is torn or damaged, allowing blood to enter false lumen divided by the flap between the inner and outer layers of the body vessel. The growth of the false lumen may eventually lead to complete occlusion of the actual artery lumen. Endoluminal device for dissection healing would reappose the dissection flap against the body vessel wall to close it off and restore blood flow through the true lumen.

Aortic aneurysms and dissection in certain regions are challenging to medically treat. For example, when such conditions occur in the ascending aorta, it has been challenging to implant endoluminal devices because there has been minimal means of securely anchoring such device in the region, which is already highly weakened and malformed from extreme enlargement. To further complicate the matter, the proximity to the aortic valve wall and large pulsatile pressure from the heart may result in device migration. A better device is needed to treat this area of the body, as well as other areas of the body.

SUMMARY

In one example, a medical device disposed about a longitudinal axis including a device body and at least one anchor element. The anchor element is coupled to the device body, and includes a thermal activatable material. The anchor element includes a first configuration and a second configuration. In the first configuration, the anchor element is disposed about an anchor axis and configured to pierce a body tissue wall. In the second configuration, in response to a temperature rise in the anchor element, the anchor element is configured to draw the pierced body tissue wall closer to the device body. The anchor axis is defined in the first configuration and is substantially perpendicular to the longitudinal axis. In response to said temperature rise, the anchor element maintains alignment substantially with the anchor axis to inhibit tearing of the pierced body tissue wall by the anchor element.

In another example, a delivery system for deployment of a prosthesis within a body vessel is provided. The system includes an outer sheath and a prosthesis. The outer sheath is coaxially disposed over an inner cannula, and the outer sheath and the inner cannula define a retention region. The prosthesis includes a prosthesis body resiliently movable between a radially compressed configuration and a radially expanded configuration, and a plurality of thermal activatable anchor elements coupled along the body. The thermal activatable anchor elements include a delivery configuration when the prosthesis is in the radially compressed configuration. When the prosthesis is in the radially expanded configuration, the thermal activatable anchor elements include a first deployed configuration and a second deployed configuration. The prosthesis is disposed along the retention region and retained in the radially compressed configuration by the outer sheath. With retraction of the outer sheath, the prosthesis is movable to the radially expanded configuration and the thermal activatable anchor elements are resiliently movable from the delivery configuration to the first deployed configuration to pierce a body tissue wall of a body vessel. In response to an increase in temperature of the thermal activatable anchor elements in the first deployed configuration, the thermal activatable anchor elements are movable to a second deployed configuration to bring the prosthesis body and the pierced body tissue wall relatively closer to one another.

In another example, a method of deploying a prosthesis within a body vessel is provided. The method includes one or more of the following steps. A step includes introducing a prosthesis into a body vessel at a treatment site. The prosthesis includes a prosthesis body and a plurality of anchor elements coupled along the prosthesis body. A step includes radially expanding the prosthesis within the body vessel such that the anchor elements are in a first deployed configuration for piercing a wall of the body vessel at the treatment site. A step includes heating the anchor elements of the radially expanded prosthesis with an inductive heating source for moving the anchor elements from the first deployed configuration to a second deployed configuration where at least a portion of the anchor elements have an enlarged configuration along an abluminal side of the pierced body vessel such that the prosthesis and the pierced body vessel wall are moved relatively closer to one another.

Other devices, systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 8 is a sectional view of a delivery and deployment system and its handle.

FIG. 8A depicts a schematic of the system in FIG. 7 and its handle.

FIG. 9 depicts a proximal end of another delivery and deployment system for a medical device FIGS. 10A-10C depict movement of the system within a body vessel based on selective expansion of the balloons.

FIGS. 13A-13H depicts delivery and deployment of a medical device with anchor elements for medical treatment of an aneurysm.

FIGS. 14A-14E depicts delivery and deployment of a medical device with anchor elements for medical treatment of an aortic dissection.

DETAILED DESCRIPTION OF THE PREFERRED EMBODIMENTS

Medical devices for implantation within a human or animal body for repair of damaged vessels, ducts, or other physiological pathways are provided. The medical devices include at least one active anchor element for fully piercing the vessel wall. The active anchor element is retractable to pull the tissue radially inward by progressively coiling or looping the anchor wire tip upon localized heating of the anchors, such as, for example, by induced heat triggering. The potential hemorrhage in piercings by the anchor elements may be inhibited by a covering or coating of SIS or other hemorrhaging inhibiting substance or material along the medical device. To this end, the active anchor elements may be capable of safely reshaping an aneurysmal site and/or pull-back a detached outer tissue layer or dissection flap of the aorta to the tunica intima. Other body vessel, duct or pathway diseases or reshaping are possible. A delivery system for such medical device may also be provided. The delivery system may include a retractable outer sheath to cover the anchor elements during delivery within the body. Balloon membranes may be a part of the system for selective expansion and targeted radial pressure of the anchor elements outward during piercing. An induction device used with such medical devices may also be provided to provide localized thermal energy to the active anchor elements for facilitating the transformation for pulling the tissue relatively closer with the medical device. By having the balloon(s) be a part of the system, the physician may more quickly pierce the tissue with inflation of the balloon(s) within the medical device in vivo for the application of the localized heating in less steps and less time, thereby improving the procedure time and avoiding delays for healing.

In the present application, the term "proximal end" is used when referring to that end of a medical device closest to the heart after placement in the human body of the patient, and may also be referred to as inflow end (the end that receives fluid first), and the term "distal end" is used when referring to that end opposite the proximal end, or the one farther from the heart after its placement, and may also be referred to as the outflow end (that end from which fluid exits).

Medical device 10 may be any device that is introduced temporarily or permanently into the body for the prophylaxis or therapy of a medical condition. For example, such medical devices may include, but are not limited to; endovascular grafts, stent grafts, bifurcated stent grafts or assembly of a multicomponent prosthesis, stents, meshes, vascular grafts, stent-graft composites, filters (for example, vena cava filters), vascular implants, tissue scaffolds, myocardial plugs, valves (for example, venous valves), various types of dressings, endoluminal prostheses, vascular supports, or other known biocompatible devices.

Figure 1:
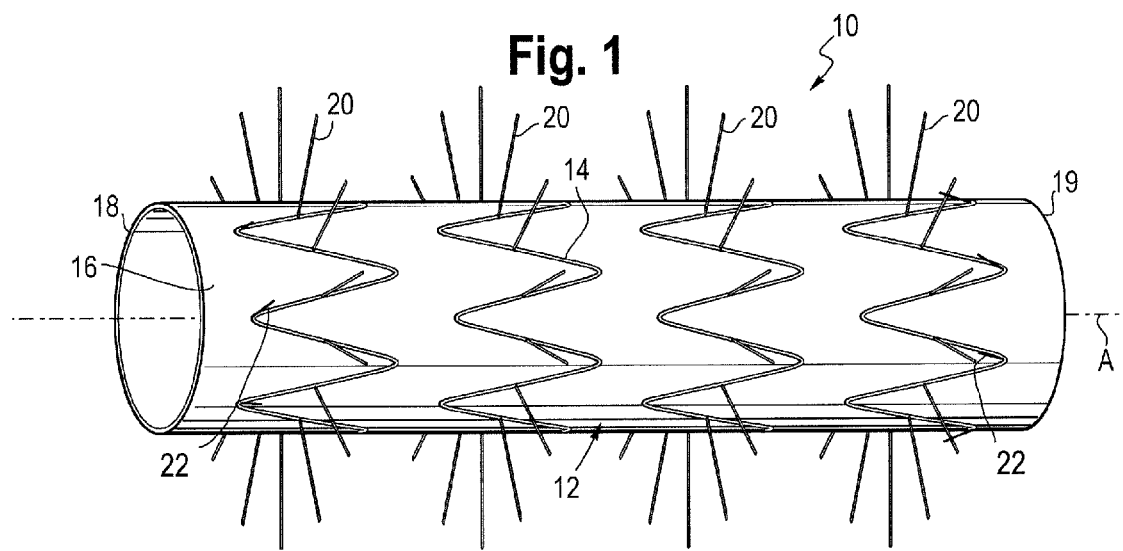
FIG. 1 is a perspective view of an example of a medical device.

Now looking more closely at the drawings, FIG. 1 depicts one example of the medical device 10 having a device body 12 and at least one anchor element 20 coupled to the device body 12. In one example, the device body 12 is shown including an expandable stent frame structure 14 (show as multiple zigzag stents). In another example, the device body 12 may include a graft covering 16 associated with the stent frame structure 14. The graft covering 16 may be configured to inhibit potential hemorrhaging of the body vessel wall from the piercings. The device body 12 is shown tubular extending along a longitudinal axis A between a proximal end 18 and a distal end 19. The device body need not be tubular and/or expandable for the active anchor elements to function. The medical device 10 may further include attachment mechanisms 22, such as, for example, barbs securely coupled to the stent frame structure 14. In one example, the stent frame structure 14 includes a proximal end and a distal end (an in some cases as shown discrete proximal and distal stents) where the attachment mechanisms 22 are located. The attachment mechanisms 22 are generally shorter than the active anchor elements and configured to partially penetrate the body vessel wall for the prevention of migration.

Figure 2:
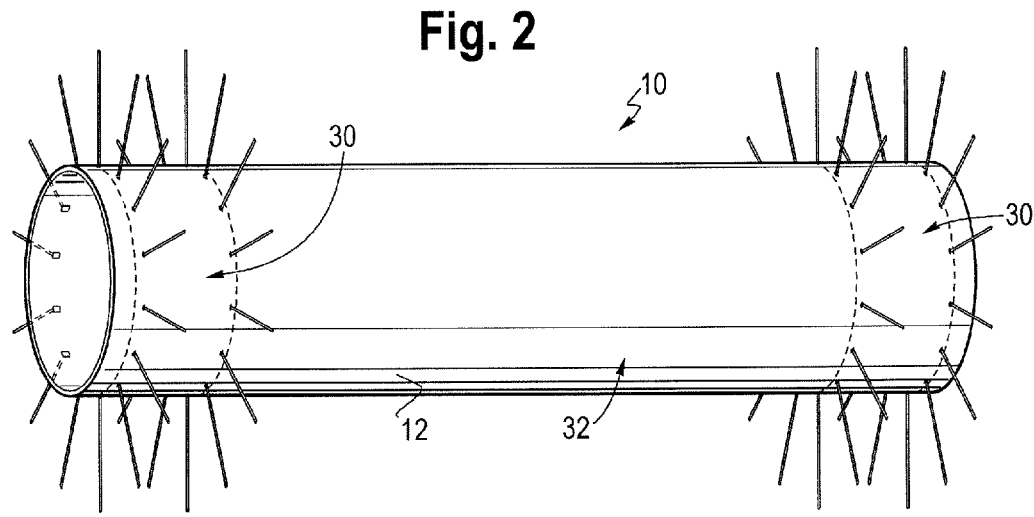
FIG. 2 is a perspective view of an example of a medical device.
Figure 3:
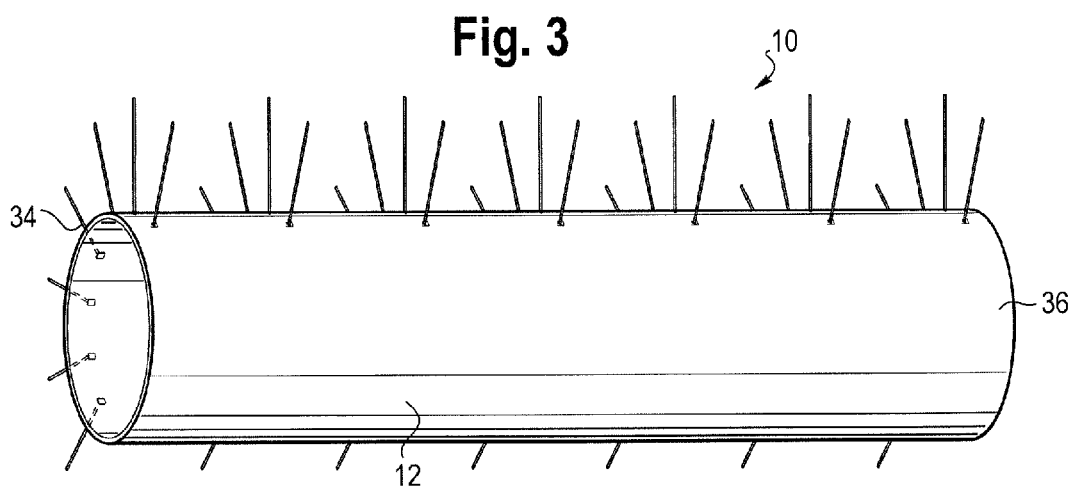
FIG. 3 is a perspective view of an example of a medical device.

It is understood from the figures that the medical device 10 may have a plurality of anchor elements 20. FIG. 1 shows the medical device 10 having the anchor elements 20 disposed along a substantial portion of the device body 12. The arrangement of the anchor elements 20 may generally disposed circumferentially and/or longitudinally around the medical device 20 to match the treatment site. In one example, the arrangement may form an annular pattern around the medical device to target 360 degrees of the body vessel wall. In one example, FIG. 2 shows the medical device 10 with two annular patterns 30 or clusters of active anchor elements 20 longitudinally spaced from one another and separated by an annular zone 32 without active anchors. In another example, the arrangement may form one or more longitudinal strips. The longitudinal strips may have a circumferential length selected from the range of about 1 to 90 degrees. A single strip may be beneficial in targeting one side of the body vessel wall. In one example, FIG. 3 shows a single longitudinal strip 34 of active anchors covering about 80 degrees of the device body 12, with a circumferential zone 36 without active anchors. The longitudinal strip 34 can be any relative length compared to the length of the device body. For example, the strip 34 is shown extending substantially across the entire length of the device body 12. Multiple strips 34 may be circumferentially disposed at angles, such as, for example, an angle of 180 degrees (for example, for two strips), 120 degrees (for example, for two or three strips), 90 degrees (for example, for two, three or four strips), 60 degrees (for example, for two, three, four, five or six strips), 45 degrees (for example, for two to eight strips), 30 degrees (for example, for two to twelve strips). Various arrangements and patterns of the anchor elements may be selected for targeting various conditions of the body vessel.

Figure 4:
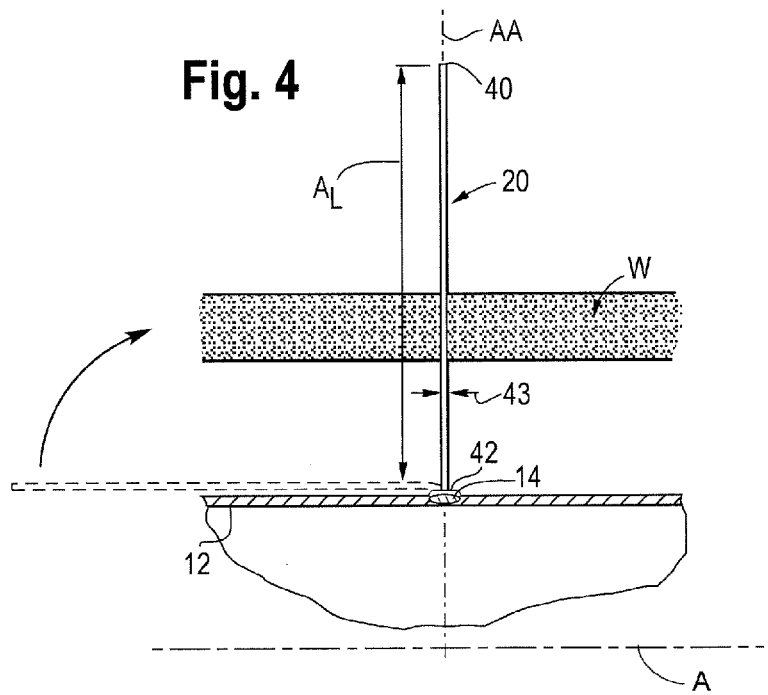
FIG. 4 illustrates an anchor element in a first deployment configuration.

FIG. 4 shows a magnified view of one of the anchor element 20. The anchor element 20 includes an anchor tip 40 and a base 42 for securely coupling to the device body 12. In one example, the anchor element 20 is a wire member and the base 42 is soldered, welded, or otherwise securely fixed to the stent frame structure 14. The anchor tip 40 is positionable to extend outwardly away from the device body 12. The base coupling may permit pivoting of the anchor element 20. In one configuration, the shape of the anchor element 20 is elongated between the anchor tip 40 and the base 42 about an anchor axis AA, which may be substantially perpendicular to the longitudinal axis A of the device body. In one example, the anchor axis defined in the first configuration is selected within a range of 0 to 15 degrees of perpendicular relative to the longitudinal axis. In one example, the anchor axis defined in the first configuration is selected within a range of 0 to 5 degrees of perpendicular relative to the longitudinal axis. The degree of perpendicularity may minimize longer cuts than necessary within the body tissue. The cross-sectional shape and size of the anchor element 20 may be configured for piercing of the body tissue wall. The wire thickness may be sized to be no larger than the critical diameter at which hemorrhaging could be greater than normal. For example, the wire thickness may be selected from the range of 0.006 to 0.012 inches (0.15 to 0.3 mm). The anchor tip 40 may be shaped with a sharp pointed tip to allow easier penetration into the body tissue wall. In one example, the anchor tip 40 may have a dull tip configured for penetrating the body tissue wall and less likely to pierce unintended body tissues after piercing through the relevant body tissue wall. At least a partial number of anchor elements 20 may have the same anchor length AL. The anchor length AL may be selected based on the profile and relative dimensions of the diseased body vessel. It is contemplated that at least a partial number of anchor elements 20 have different lengths (see, for example, FIG. 13C), depending the shape of the diseased body vessel wall and for careful piercing of the body vessel wall. For example, a large aneurysm may exceed 5.5 cm diameter for a 2 cm aorta, and in such environment, the anchor length AL may be selected from the range of 20 mm to 30 mm. For smaller aneurysms, the anchor length AL may be smaller For dissections, the aortic wall thickness may be about 1.6 mm, and in such environment, the anchor length AL may be selected from the range of 3 mm to 10 mm.

The anchor element 20 comprises a thermal activatable material, such as, for example, a shape memory material, such that the anchor element may include multiple configurations for delivery and deployment. In one example, the thermal activatable material anchor element has two defined geometries for deployment. The anchor element may have delivery configuration. In the delivery configuration, the anchor element 20 may be positioned in a manner to reduce the overall profile of the medical device, which is shown in FIG. 9. The delivery configuration of the anchor element is also shown in dashed lines in FIG. 4.

The anchor element 20 made of a thermal activatable wire material may be biased into a straight elongated geometry having a first cross-sectional area 43 and shape in a first deployment configuration at a first temperature range, as shown in FIG. 4. The first temperature range being controlled, for example, by room temperature and by the body temperature and blood temperature across the medical device. In the first deployment configuration, the anchor element is disposed extending radially or laterally outward along the anchor axis AA for piercing the body tissue wall. The first cross-sectional area 43 may match the cross-sectional area of piercing within the body tissue wall W (shown in dashed lines).

Figure 5:
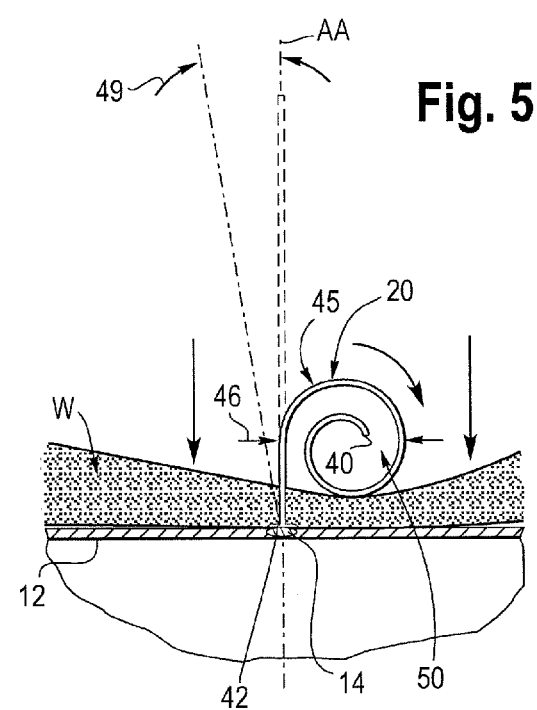
FIG. 5 illustrates the anchor element in FIG. 4 in a second deployment configuration.

At a second temperature, greater than the first temperature range, such as provided by localized temperature increase within the anchor element 20 either from external to the body or inside the vessel, the anchor element 20 changes from its biased configuration to a second deployment configuration, as shown in FIG. 5. In one example, as will be described, an external induction device may provide targeted and localized heating of the anchor elements 20. Such induction device may provide thermal energy electromagnetically. Other means for providing thermal energy to the anchor elements will be described.

In the second deployment configuration, the anchor element 20 includes an enlarged portion 45 having a second cross-sectional area 46 and shape. The transformation of the anchor element shape between the first and second deployment configurations places the anchor tip 40 and the enlarged portion 45 relatively closer to the device body 12. The enlarged portion 45 may be spaced from the base 42 by a distance of body vessel wall W thickness. For example, in response to a temperature rise in the anchor element 20, during the transformation to the second deployment configuration, the enlarged portion 45 of the anchor element 20 draws the pierced body tissue wall W closer to the device body 12, as shown, for example, in FIGS. 13F-13G. During the drawing action, the anchor element 20 is configured to maintain alignment substantially with the anchor axis AA. Maintaining the alignment in the second deployment configuration may inhibit the anchor element moving or pivoting extremely within the pierced opening in the body vessel wall W that may result in tearing of the pierced body tissue wall by the anchor element. In one example, the anchor element 20 may be permitted to move or pivot substantially within an angle 49 of 15 degrees of the anchor axis AA relative to the coupled base 42. In another example, the angle 49 may be up to 10 degrees, and in yet another example, the angle 49 may be in the range of 0 to 5 degrees.

Figure 6A:
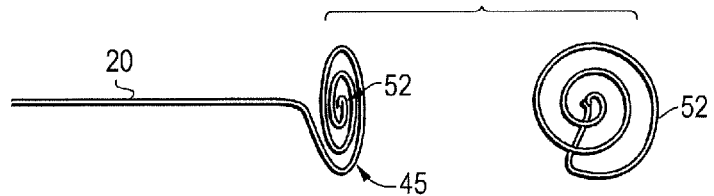
FIG. 6A-6F depict various second deployment configurations of the anchor element.
Figure 6B:
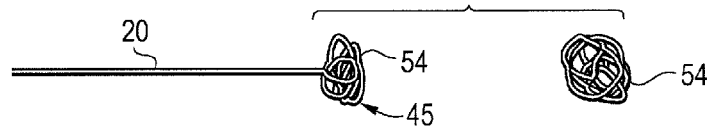
Figure 6C:
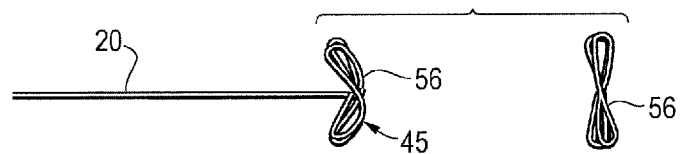
Figure 6D:
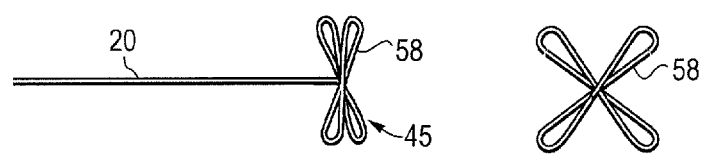
Figure 6E:
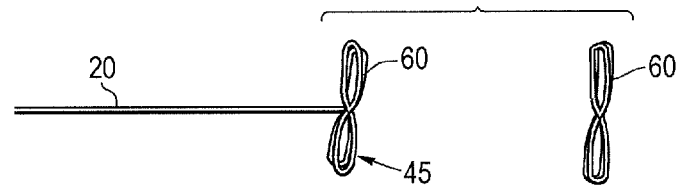
Figure 6F:
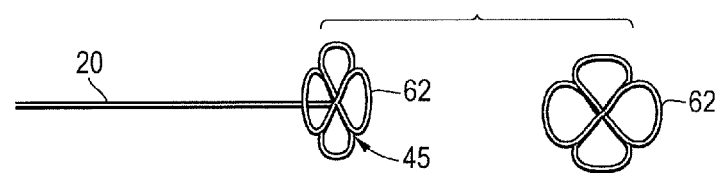

The enlarged portion 45 may be formed into a variety of shapes. FIG. 5 shows on configuration of a coiled shape 50 where the anchor tip begins winding in a manner where the radial and longitudinal profile of the wound enlarged portion are increased. FIGS. 6A-6F show other enlarged portion shapes. FIG. 6A shows a enlarged portion configuration of a coiled shape 52 where the anchor tip 40 begins winding in a manner where the circumferential and/or radial profile of the wound enlarged portion 45 is increased. FIG. 6B shows an enlarged portion configuration of an irregular coiled or loop shape 54 where the anchor tip begins winding and/or looping in an irregular manner for a blob shape where the radial and circumferential profile of the wound enlarged portion are increased. FIG. 6C shows an enlarged portion configuration of a loop wing shape 56 where the anchor tip 40 begins looping in a manner to form an angled winged profile where the circumferential and/or radial profile of the winged enlarged portion 45 is increased. FIG. 6D shows an enlarged portion configuration of a loop cross shape 58 where the anchor tip 40 begins looping in a manner to form an angled cross profile where the circumferential and/or radial profile of the winged enlarged portion 45 is increased. FIG. 6E shows an enlarged portion configuration of a looped shape 60 where the anchor tip 40 begins looping in a manner to form a propeller or figure eight where the circumferential and/or radial profile of the enlarged portion 45 is increased. FIG. 6F shows an enlarged portion configuration of a looped shape 62 where the anchor tip 40 begins looping in a manner to form three or more petals where the circumferential and/or radial profile of the enlarged portion 45 is increased. In one example, the enlarged portion 45 is shaped having a coiled or looped configuration.

When considering the various arrangements, the anchor elements 20 may have a common first and second deployment configuration size and shape. In another example, at least one anchor element 20 may have a different first deployment configuration and/or second deployment configuration size and shape relative to other anchor elements. For example, a portion of the anchor elements 20 may not be made of the thermal activatable material and thus may only have the delivery configuration and the first deployment configuration. In another example, the shape and position of the enlarged portion 45 may vary across the anchor members 20 depending on their relative location along the body vessel wall, when such differences may be beneficial for enhanced anchoring capability.

As discussed above, the thermal activatable material, such as, for example, a shape memory material may be use for the anchor elements 20. The shape memory material may be at least one of a metal, a metal alloy, a nickel titanium alloy, and a shape memory polymer. Shape memory alloys have the desirable property of becoming rigid, that is, returning to a remembered state, when heated above a transition temperature. A shape memory alloy suitable for the present invention is Ni—Ti available under the more commonly known name Nitinol. When this material is heated above the transition temperature, the material undergoes a phase transformation from martensite to austenite, such that material returns to its remembered state. The transition temperature is dependent on the relative proportions of the alloying elements Ni and Ti and the optional inclusion of alloying additives. In one embodiment, the anchor element is made from Nitinol with a austenite start temperature (As) and austenite finish temperature (Af), for example, 104° F. to 176° F. (40° C. to 80° C.) that is higher than normal body temperature of humans, which is about 98.6° F. Thus, when the medical device 10 is deployed in a body vessel and exposed to normal body temperature, the anchor element 20 will be maintained in its first deployment configuration state. When heated, such as with inductive heating, the alloy of the anchor element 20 will transform to austenite, that is, the remembered state, into one of the shapes disclosed above for the second deployment configuration. When the inductive heating source is removed, the anchor element 20 is allowed to cool to transform the material to martensite which is more ductile than austenite, with the anchor element 20 maintaining the general shape of its austenite state.

As generally understood by those skilled in the art, martensite start temperature refers to the temperature at which a phase transformation to martensite begins upon cooling for a nickel-titanium shape memory alloy, and martensite finish temperature refers to the temperature at which the phase transformation to martensite concludes. Austenite start temperature (As) refers to the temperature at which a phase transformation to austenite begins upon heating for a nickel-titanium shape memory alloy, and austenite finish temperature (Af) refers to the temperature at which the phase transformation to austenite concludes.

The thermal activatable material, such as, for example, a shape memory material alloy, may be cold worked into desired anchor element shapes (e.g., shapes associated with the second deployment configuration described above) by, for example, drawing, rolling, or another forming method. Mandrels with posts may be used for the various coil and/or looped patterns described herein. The cold working typically involves several forming passes in combination with inter-pass annealing treatments at temperatures in the range of from about 600° C. to about 800° C. The interpass annealing treatments soften the material between cold work passes, which typically impart 30-40% deformation to the material. Machining operations, such as, for example, drilling, cylindrical centerless grinding, or laser cutting may also be employed to fabricate the desired component (e.g., the sharp or dull tipped anchors). A heat treatment may be employed to impart a "memory" of a desired high temperature shape and to optimize the shape memory/superelastic and mechanical properties of the anchor element. The number, duration and the temperature of the heat treatments may affect the transformation temperatures. Typically, heat treatment temperatures of 400° C. to 550° C. may be appropriate to set the final shape and to optimize the properties.

Anchor elements 20 may be may be made of shape memory alloys, such as, for example, ferromagnetic materials, that respond to changes in magnetic field. Anchor elements made from a ferromagnetic shape memory effect transforms from the martensite phase where the anchor elements are in the first deployment configuration to the austenite phase where the anchor elements are in the second deployment configuration when exposed to an external magnetic field. The term "ferromagnetic" as used herein is a broad term and is used in its ordinary sense and includes, without limitation, any material that easily magnetizes, such as a material having atoms that orient their electron spins to conform to an external magnetic field. Ferromagnetic materials include permanent magnets, which may be magnetized through a variety of modes, and materials, such as metals, that are attracted to permanent magnets. Ferromagnetic materials also include electromagnetic materials that are capable of being activated by an electromagnetic transmitter, such as one located external to patient. Ferromagnetic materials may include one or more polymer-bonded magnets, wherein magnetic particles are bound within a polymer matrix, such as a biocompatible polymer. The magnetic materials can comprise isotropic and/or anisotropic materials, such as for example NdFeB (neodymium-iron-boron), SmCo (samarium-cobalt), ferrite and/or AlNiCo (aluminum-nickel-cobalt) particles. Examples of ferromagnetic shape memory alloys include Fe—C, Fe—Pd, Fe—Mn—Si, Co—Mn, Fe—Co—Ni—Ti, Ni—Mn—Ga, Ni2MnGa, Co—Ni—Al, and the like. Certain of these shape memory materials may also change shape in response to changes in temperature. Thus, the shape of such materials can be adjusted by exposure to a magnetic field, by changing the temperature of the material, or both.

Figure 7:
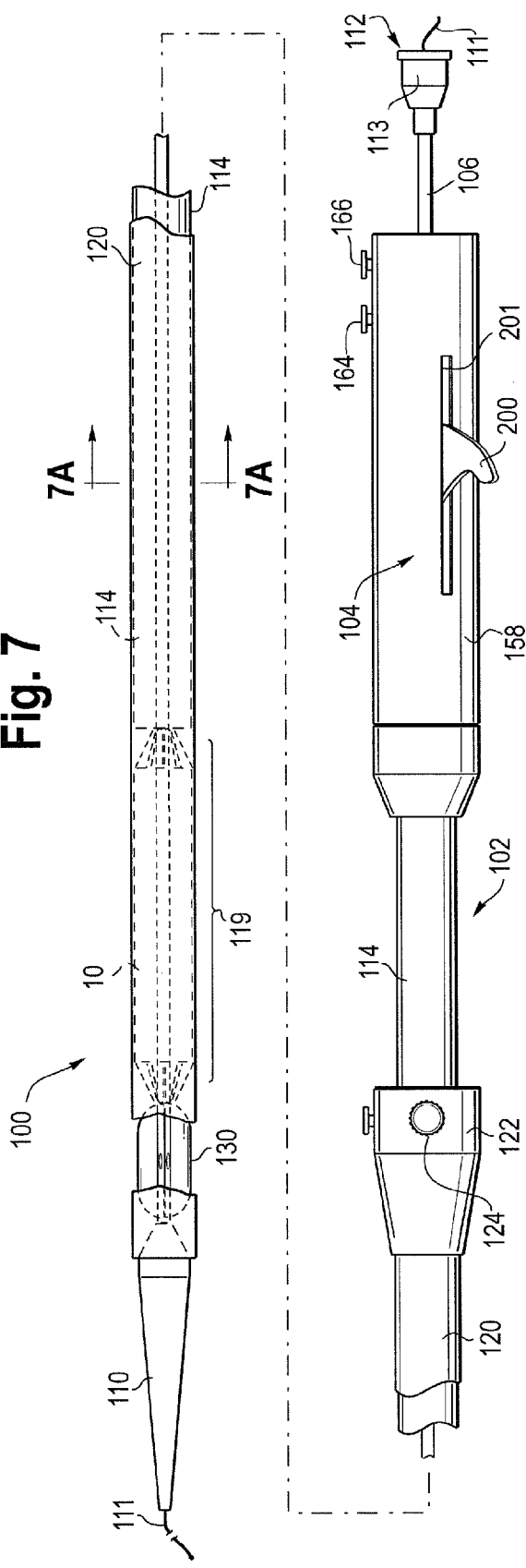
FIG. 7 depicts a delivery and deployment system for a medical device.

FIGS. 7-8 show one example of a delivery and deployment system 100. In FIG. 7, the system 100 includes a catheter body 102 extending proximally from a handle 104. The catheter body 102 including an inner cannula 106 extending from the handle 104 having a proximal end coupled to a nose cone dilator 110. The inner cannula 106 includes a longitudinal guide wire passage 112 to allow the system to receive a guide wire 111 and track along the guide wire 111. The distal end of the inner cannula 106 may have a fluid coupling device 113 operable to receive a fluid source. A pusher device 114 may be slidably coupled to the inner cannula 102. The pusher device 114 extends along a substantial distal portion of the inner cannula 106 and terminates short of the dilator 110 to define a device retention longitudinal region 119 sized to receive the medial device 10 in a crimped compressed state. A retractable outer sheath 120 is coaxially disposed over the inner cannula 106 and pusher device 114. The outer sheath 120 may include a sheath hub 122 at its distal end 123. The sheath hub 122 may include an attachable device 124, such as a screw, configured for locking and free the relative position of the outer sheath relative to the pusher device. In a sheath delivery configuration, the outer sheath 120 is disposed over the loaded device 10 to maintain the device in the compressed profile, as shown in FIG. 7. In a sheath deployed configuration, the outer sheath 120 is moved distally relative to the device 10 to allow the device 10 to move from the compressed profile to a radially expanded configuration, as shown in FIG. 13C. Although not shown, proximal and distal retention devices may be applied to the medical device 10 that may be released with corresponding trigger devices from the handle 104. Such retention devices may allow for repositioning of the medical device prior to full expansion.

In example, the system 100 includes at least one inflatable balloon membrane 130 disposed at the proximal region of the inner cannula 106 to define one or more balloons. A dual-balloon device configuration will be described in detail, and it is understood that additional balloons may be similarly applied to the system for more accurate targeting. One such balloon device having four balloons that may be utilized is described in U.S. Patent Application Publ. 2008/0103443 to Kabrick et al. filed Oct. 26, 2007, assigned to Cook Incorporated, which is incorporated herein in its entirety.

Figure 7A:
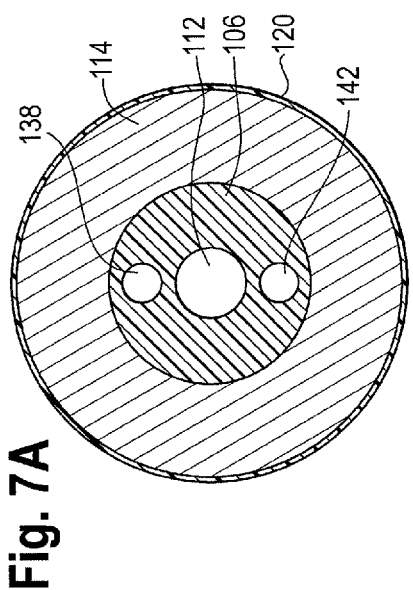
FIG. 7A is a transverse cross-sectional view of the system, taken along lines 7A-7A in FIG. 7.

In one example shown in FIG. 8, at least one inflatable balloon membrane 130 includes a first inflatable balloon 132 and a second inflatable balloon 134 are disposed in a longitudinal side-by-side relationship at the proximal end of the inner cannula 106. The inner cannula 106 may include a first inflation side port 136 and a first inflation lumen 138 in communication with one another formed in the inner cannula 106. The first balloon membrane 130 is positioned over the first inflation side port 136 and sealed accordingly along the inner cannula 106. The inner cannula 106 may include a second inflation side port 140 and a second inflation lumen 142 in communication with one another formed in the inner cannula 106. The second inflation side port 140 may be circumferentially disposed away from the first inflation port 136. The second inflation lumen 142 may be independent and separate from the first inflation lumen 140, as shown in FIG. 7A. The second balloon membrane 132 is positioned over the second inflation side port 140 and sealed accordingly along the inner cannula 106.

Inflation fluid may be introduced into the inflation lumens 138, 142, such as, for example, distal ends 150, 152 of respective inflation lumens 138, 142. The inflation fluid traverses through the inflation lumens 138, 142 and exits the respective side ports 136, 140 to fill the corresponding balloon membranes 130, 132. The independent expansion and variable radial cross-sectional areas of the first balloon 130 and the second balloon 132 permits relative positioning of the catheter body within the body vessel, such as, for example, shown in FIGS. 10A-10C. In one example, in response to expansion of the balloons 130, 132, the catheter body may be positioned approximately in the center of the body vessel (see FIG. 10C). By varying the inflation fluid and pressure in one or each of the balloons 130, 132, the catheter body may be positioned eccentrically or offset from the center of the body vessel (see FIGS. 10A-10B). The balloon membranes 130, 132 may be bonded or attached to the inner cannula using an adhesive, such as a biocompatible glue, or alternatively, using heat-shrink tubing, heat bonding, laser bonding, welding, solvent bonding, or the like. The balloons may be cylindrically shaped having longitudinal length greater than its width, but may also have other shapes such as, for example, circular, oval, tapered or the like. The balloon membrane material may be any known balloon material, such as, for example, PEBAX, nylon, Hytrel, Arnitel or other polymers suitable for use.

With reference to FIG. 7 and FIG. 8A, the handle 104 may be configured for delivery inflation fluid from an external source to within the balloon(s). The handle 104 is shown having a body 158 defining a cavity 160 and housing a fluid reservoir 162. The handle body 158 may be made of a biocompatible material, such as a thermoplastic or molded plastic material. One or more ports (two ports 164, 166 shown) are disposed on the wall of the handle body 158. The inlet port 164 may be configured for fluidly coupling to an inflation fluid source, such as, for example, a syringe. The inlet port 164 may be configured for fluidly coupling to a contrast agent source, such as, for example, a syringe. The exhaust port 166 is provided to remove any air in the system as fluids are introduced. One or both inlet ports 164, 166 may be fluidly coupled with the fluid reservoir 162 via a fluid passage (two passages 170, 172 shown) formed in the handle 104. A valve 174 may be coupled between the passages 170, 172 and the fluid reservoir 162. The valve body having two inlets and a single outlet and a movable valve membrane between the inlets and outlet to fluidly couple one of the inlets with the outlet. The valve 174 may be operable external to the handle cavity 160 between a first position to couple the port 164 to the fluid reservoir 162 and a second position to couple both ports 164 to the fluid reservoir. Valve may also be moveable to a closed position to decouple the ports from the fluid reservoir.

Outlet ports (two outlet ports 180, 182 shown) are disposed on the wall of the handle body 158. One or both outlet ports 180, 182 may be fluidly coupled with the fluid reservoir 162 via a fluid outlet passage (two outlet passages 184, 186 shown) defined within the handle body 158. The outlet ports 180, 182 may be configured for fluidly coupling the respective inflation lumens 138, 142 to the corresponding fluid outlet passages 184, 186.

The fluid reservoir 162 may include a first chamber 190 and a second chamber 192 separated from another via a piston 194 in slidably sealable contact along the inner walls 196 of the fluid reservoir 162. The first chamber 190 is in fluid communication with the first balloon 130 via the first fluid outlet passage 184, the first outlet port 180, the first inflation lumen 138 and the first inflation side port 136. The second chamber 192 is in fluid communication with the second balloon 132 via the second fluid outlet passage 186, the second outlet port 182, the second inflation lumen 142 and the second inflation port 140. Slidable movement of the piston 194 within the inflation fluid reservoir 162 selectively increases or decreases fluid volumes of the respective first and second chambers 190, 192. In one example, the piston 194 is coupled to an operable lever 200 externally disposed relative to the handle body 158. The operable lever 200 may be slidably disposed within an elongated slot 201 formed in the handle body 158. The walls defining the slot 201 guide the movement of the lever 200.

FIGS. 10A-10C depict movement of the catheter body 102 within the body vessel based on independent expansion of the balloons 130, 132. The use of multiple balloons allow targeted radial pressure of the medical device 10 at the treatment site, for example, in the case of aneurysmal or dissection associated non-symmetric enlargement of the body vessel lumen.

In an example when the first and second balloons 130, 132 have a common volume and/or expansion cross-sectional area and the first and second chambers 190, 192 have a common volume, the operable lever 200 moved in the proximal direction operably moves the piston 194 within the fluid reservoir 162 in the proximal direction P to reduce the volume of the first chamber 190, which increases the cross-sectional area of expansion of the first balloon 130, and to increase the volume of the second chamber 192, which reduces the cross-sectional area of expansion of or deflates the second balloon 132. The lever 200 at this proximal position brings the catheter body 102 away from the body vessel center eccentrically to a first side of the body vessel wall, as shown in FIG. 10A. The operable lever 200 moved in the distal direction D operably moves the piston 194 in the distal direction to reduce the volume of the second chamber 192, which increases the cross-sectional area of expansion of the second balloon 132, and to increase the volume of the first chamber 190, which reduces the cross-sectional area of expansion of or deflates the first balloon 130. The lever 200 at this distal position brings the catheter body 102 away from the body vessel center eccentrically to an opposite, second side of the body vessel wall, as shown in FIG. 10B. The operable lever 200 moved in the center of travel operably moves the piston 194 in the center of the fluid reservoir 162 to equalize the volumes of the first and second chambers 190, 192, which equalizes the cross-sectional area of expansion of the first and second balloons 130, 132. The lever at this center position brings the catheter body 102 to the center of the body vessel, as shown in FIG. 10C. When the first and second balloons have a different volume and/or expansion cross-sectional area, the lever may be positioned at a position other than center for equalized expansion. In another example, the first and second chambers may have different volumes.

In one example, the at least one balloon is disposed proximal to the loaded medical device, such as shown in the illustrations in FIG. 8A and FIGS. 10A-10C. Retention devices around the loaded medical device 10 may remain on during expansion of the balloons 130, 132 for targeting the medical device within the body vessel lumen. When the medical device is positioned accurately, the retention devices may be released to allow for full self-expansion of the medical device. When the anchor elements of the expanded medical device are in the first deployment configuration, the balloon may be repositioned within the expanded medical device. After repositioning, selective inflation of the balloons applies targeted radial pressure from within the radially expanded prosthesis to urge the anchor element further within and fully through the body tissue wall.

The at least one balloon may be at least partially disposed within the loaded medical device, as shown in FIGS. 8-9. In one example, a proximal region of the balloons 130, 132 is shown extended beyond the proximal end 18 of the loaded medical device 10, and a distal region of the balloons 130, 132 is shown extending along the inner surface of at least a proximal region of the medical device 10. In one example, the balloons 130, 132 are fully disposed within the loaded medical device without a proximally extended region. The outer sheath 120 is fully retracted in the direction of the arrow from the medical device 10 to allow full self-expansion of the medical device 10. When the anchor elements 20 of the expanded medical device 10 are in the first deployment configuration, selective inflation of the balloons 130, 132 applies targeted radial pressure from within the radially expanded medical device 10 to urge the anchor elements 20 farther within and fully through the body tissue wall.

Figure 11:
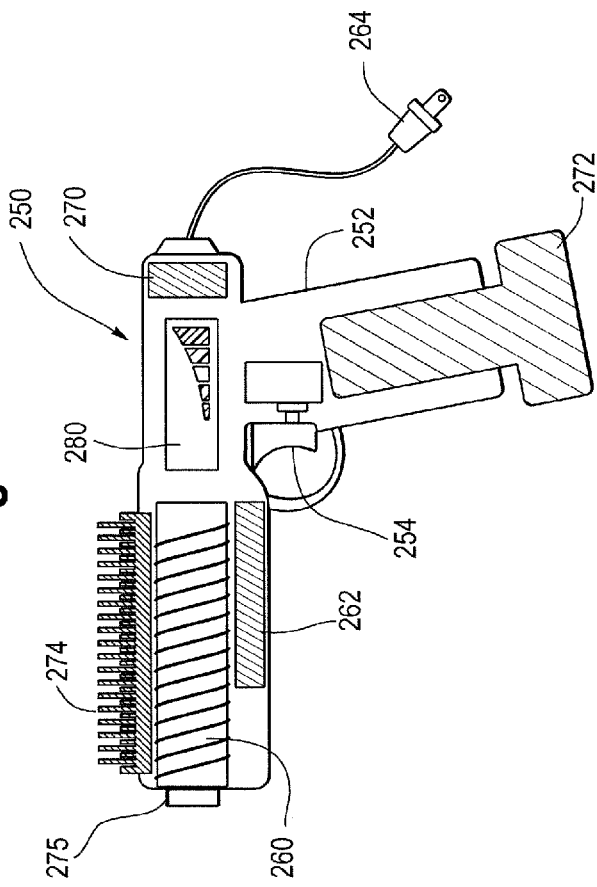
FIG. 11 illustrates an induction device that may be used with the medical device.

FIG. 11 illustrates one example of an external, non-invasive induction device 250 for use with the system 100. The induction device 250 is operable to provide targeted and localized heating of the anchor elements 20. Such induction device 250 may provide thermal energy electromagnetically. The anchor element 20 may be transform to the second deployment configuration in response to be heated with at least one of a magnetic resonance imaging energy, ultrasound energy, radio frequency energy, x-ray energy, microwave energy, light energy, electric field energy, magnetic field energy, inductive heating, and conductive heating.

The induction device 250 may include a handheld or portable body 252 for grasping the device and a trigger switch 254 for selectively activating and deactivating an electromagnetic field (EMF) energy. The EMF energy may be focused to provide directional heating to the active anchor elements 20 of the medical device 10. Housed within the body is an electromagnetic field energy (EMF) generator 260 to generate the EMF energy field that penetrates the body of the patient and induces a current within the active anchor element 20 to a treatment site within a patient to perform the medical procedure. The EMF generator 260 may include an electrically conductive coil. The induced current within the anchor elements 20 is suitable to heat the active anchor element and cause the thermal activatable material to transform from the first deployment configuration to the second deployment configuration.

An electrical controller 262 may be housed within the body 252. The controller 262 may be in electrical communication with the trigger switch 254, a power supply 264, and the EMF generator 260. The controller 262 may generally include a processor and a memory. The memory may retrievably store one or more algorithms, data, predefined relationships between different induction device parameters, preprogrammed models, such as in the form of lookup tables and/or maps, or any other information that may be accessed by the controller and relevant to the operation of the induction device. The body housing of the controller 262 may be an enclosed structure that is configured to house circuitry and/or various circuit elements that measure the EMF energy and determine when the EMF energy reaches a predetermined level. The circuits may be hardware and/or analog circuits comprised of analog components that perform analog operations. In one example, at least some of the circuits may include digital circuitry, such as microprocessors, microcontrollers, integrated circuits, digital hardware logic, or other similar types of digital circuits configured to perform digital operations and/or execute software to perform energy measurement and timing operations. Switching circuitry may be included in the controller 262 and configured to pulsate the EMF generator 260. Pulsating the EMF generator 260 may provide better control of the thermal energy being delivered and the induced current heating the active anchor elements 20. The anchor elements 20 may be selectively heated using short pulses of EMF energy having an on and off period between each cycle. The energy pulses provide segmented heating.

Blocking and matching circuitry may be included with the controller 262. The matching circuitry may be configured to match the impedance of the output load and the output impedance of the EMF generator 260. The blocking circuitry may be configured to prevent direct current and/or low frequency components of the EMF energy from being communicated to the output. The controller 262 may also include energy measurement circuitry and/or logic to determine an amount of energy and to compare with a threshold energy level, so that the energy may be cut off or ramped up. The controller 262 may include power circuitry to control for power the circuitry and the generator. The power circuity electrically coupled to the power supply 264, such as a 120 volt AC source, a step down transformer and AC modulator 270. The power circuity may include a battery power source 272 that may be operably coupled to the circuitry and/or the 120 volt AC source for charging. A heat sink 274 may be provided to regulate heating of the induction device. An insulator 275 may be provided at the tip of the induction device to inhibit electrical energy of the induction device from direct contact to the patient's body.

The controller 262 may measure the EMF energy being delivered to the treatment site and determine when the EMF energy reaches a predetermined level. When the EMF energy reaches the predetermined energy level, the controller 262 may inhibit further EMF energy from being delivered to the medical device. The predetermined EMF energy level may be a selected amount of energy to be delivered to the treatment site for performing the medical procedure. When more than the predetermined EMF energy level is delivered, harm or injury may be caused to the patient, such as burning of tissue at the treatment site. Alternatively, when less that the predetermined EMF energy level is delivered, the medical procedure may be unsatisfactorily performed, such as by failing to pull the tissue relatively closer to the implanted medical device. As such, the controller 262 may be and/or provide a control and safety mechanism for the EMF generator.

The device housing body 252 may include an indicator 280, and the controller 262 may include an indication circuitry configured to output an indication of EMF energy being supplied to the medical device 10. In one example embodiment, the indication circuitry includes a light emitting diode (LED) or liquid crystal displace (LCD) that outputs a light signal or is "on" when the EMF signals are being sent and does not output a light signal or is "off" when EMF energy is not being supplied. In alternative example embodiments, the indication circuitry may include circuitry in addition to or other than an LED, such as speaker or a display device that outputs an audio and/or a visual signal to indicate whether EMF energy is being supplied to the medical device. The indication circuitry may be useful to and/or used by an operator of the EFM generator, which may identify when to cease application of the EMF energy (e.g., by removing finger off of trigger switch) by observing the indication, such as when the LED turns from "on" to "off."

The term "graft" describes an object, device, or structure that is joined or that is capable of being joined to a body part to enhance, repair, or replace a portion or a function of that body part. Grafts that can be used to repair body vessels include, for example, films, coatings, or sheets of material that are formed or adapted to conform to the body vessel that is being enhanced, repaired, or replaced. The graft material may include a biocompatible synthetic or biomaterial. Examples of suitable synthetic materials include fabrics, woven and nonwoven materials, and porous and nonporous sheet materials. Other synthetic graft materials include biocompatible materials such as polyester, polytetrafluoroethylene ("PTFE"), polyurethane ("PU"), fluorinated ethylene propylene ("FEP") and the like. Examples of suitable biocompatible materials include, for example, pericardial tissue and extracellular matrix materials ("ECMM") such as SIS.

Other synthetic materials, such as biocompatible synthetic materials, may be used for the graft material. Synthetic materials may include polymers such as, for example, poly (urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly (methacrylic acid), polylactides ("PLA"), polyglycolides ("PGA"), poly(lactide-co-glycolid-es) ("PLGA"), polyanhydrides, polyorthoesters or any other similar synthetic polymers that may be developed that are biocompatible. Biocompatible synthetic polymers also may include copolymers, blends, or any other combinations of the forgoing materials either together or with other polymers generally. The use of these polymers will depend on given applications and specifications required. Suitable polymer material may include, for example, polyester such as DACRON™, polyetherurethanes such as THORALON® from Thoratec Corporation (Pleasanton, Calif.), or polyethylene terephthalate ("PET").

In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. Thus, any polymer that may be formed into a porous sheet can be used to make a graft material, provided the final porous material is biocompatible. Polymers that can be formed into a porous sheet include polyolefins, polyacrylonitrile, nylons, polyaramids and polysulfones, in addition to polyesters, fluorinated polymers, polysiloxanes and polyurethanes as listed above. Preferably the porous sheet is made of one or more polymers that do not require treatment or modification to be biocompatible.

The graft material, the coating, or one class of materials for electrospinning may also include extracellular matrix materials. The "extracellular matrix" is typically a collagen-rich substance that is found in between cells in animal tissue and serves as a structural element in tissues. Such an extracellular matrix is preferably a complex mixture of polysaccharides and proteins secreted by cells. The extracellular matrix can be isolated and treated in a variety of ways. Following isolation and treatment, it is referred to as an "extracellular matrix material," or ECMM. ECMMs may be isolated from submucosa (including small intestine submucosa), stomach submucosa, urinary bladder submucosa, tissue mucosa, renal capsule, dura mater, liver basement membrane, pericardium or other tissues.

The stent or support frame structures may be any device or structure that provides or is configured to provide rigidity, expansion force, or support to a body part, for example, a diseased, damaged, or otherwise compromised body lumen. Such stent frame structure may include any suitable biocompatible material, including, but not limited to fabrics, metals, plastics, and the like. Examples of suitable materials include metals such as stainless steel and nitinol, and plastics such as PET, PTFE and polyurethane. The stent frame structure may be "expandable," that is, it may be capable of being expanded to a larger-dimension configuration. The stent frame structure may expand by virtue of its own resilience (i.e., self-expanding), upon the application of an external force (i.e., balloon-expandable), or by a combination of both. In one example, the stent frame structure may have one or more self-expanding portions and one or more balloon-expandable portions. The stent struts that are interconnected to one another represents specific configurations of a wire member that comprises a basic structural component of the stent. As used herein, the term "wire" refers to any filamentary member, including, but not limited to, drawn wire and filaments that have been laser cut from a cannula. For example, the stent architecture with the intricate mating elements that form the interlocking joints may lend itself to being manufacture from a metal cannula laser cut to the desired pattern as described. The shape, size, and dimensions of the stent structure may vary. The size of these components and the overall stent structure is determined primarily by the diameter of the vessel lumen at the intended implant site, as well as the desired length of the overall stent device. The stent structure and/or ring structures may have a common cross-sectional area along the body or may vary to have different cross-sectional areas.

Figure 12:
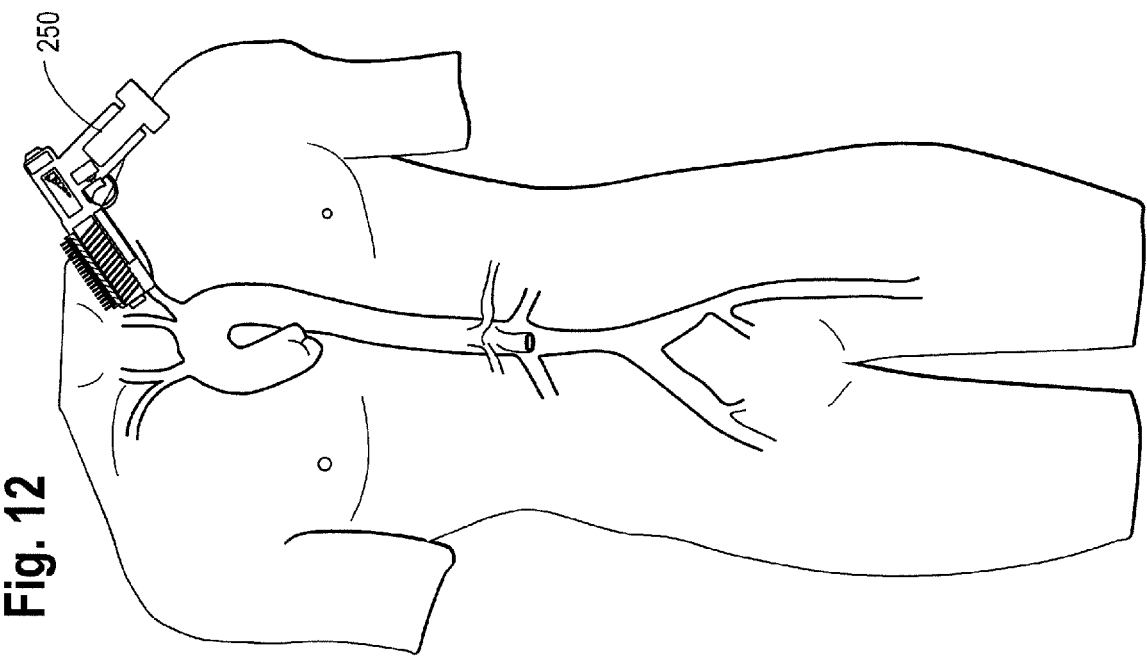
FIG. 12 depicts the relative position of the induction device when treating the aorta.

FIG. 12 depicts placement of the induction device externally along the body and oriented at the appropriate body vessel for treatment, such as the ascending aorta. Methods of deploying any one of the medical devices described herein, such as by placing a medical device 10 described herein into a body at a point of treatment with the system. The medical device 10 may be delivered with suitable techniques, depending on the type of medical device. In one example, access to the body may be attained by inserting an access device, such as an introducer sheath, into the body passageway. One typical procedure for inserting the introducer sheath over an inserted guide wire using the well-known Seldinger percutaneous entry technique.

Figure 13B:
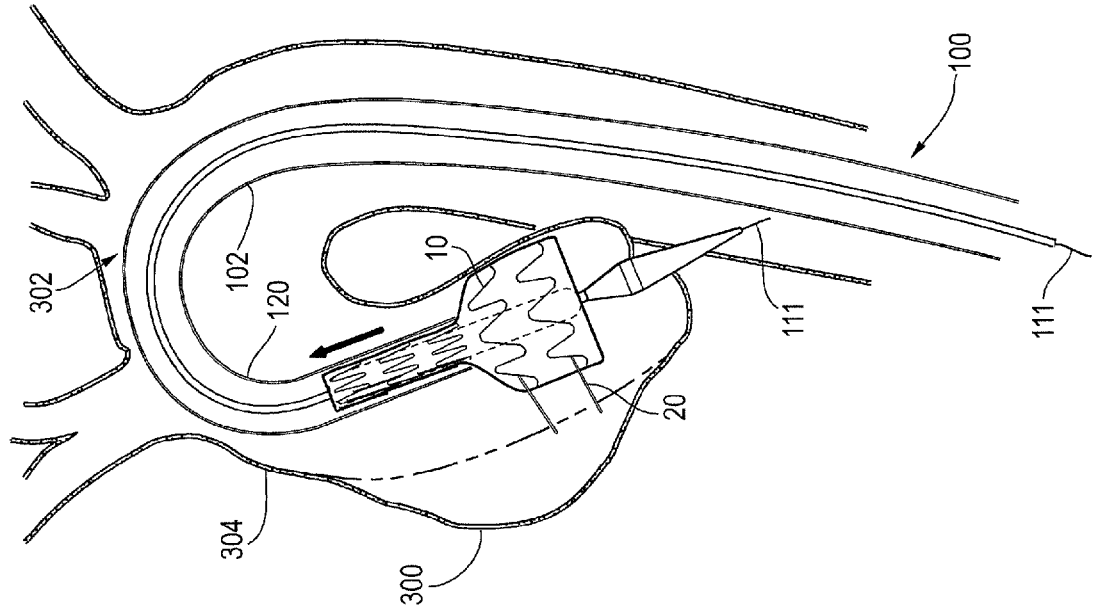
Figure 13A:
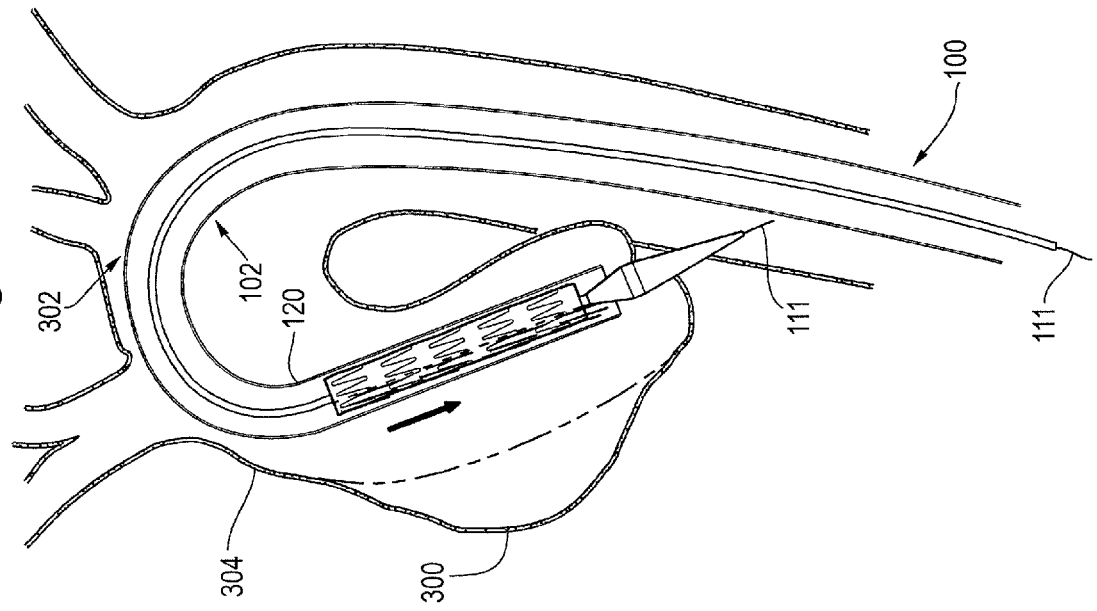
Figure 13D:
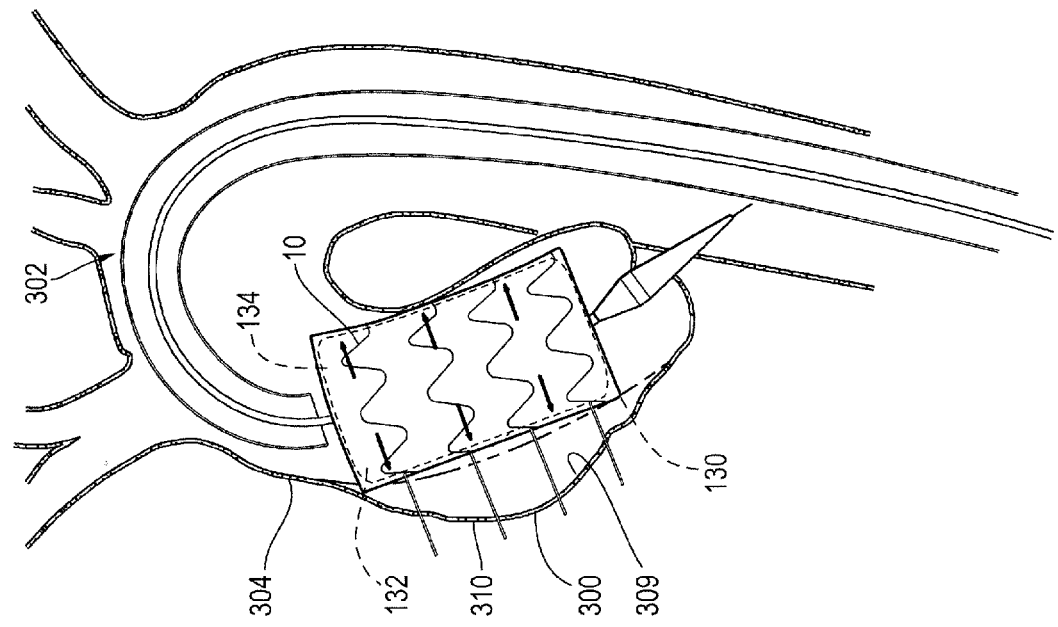
Figure 13C:
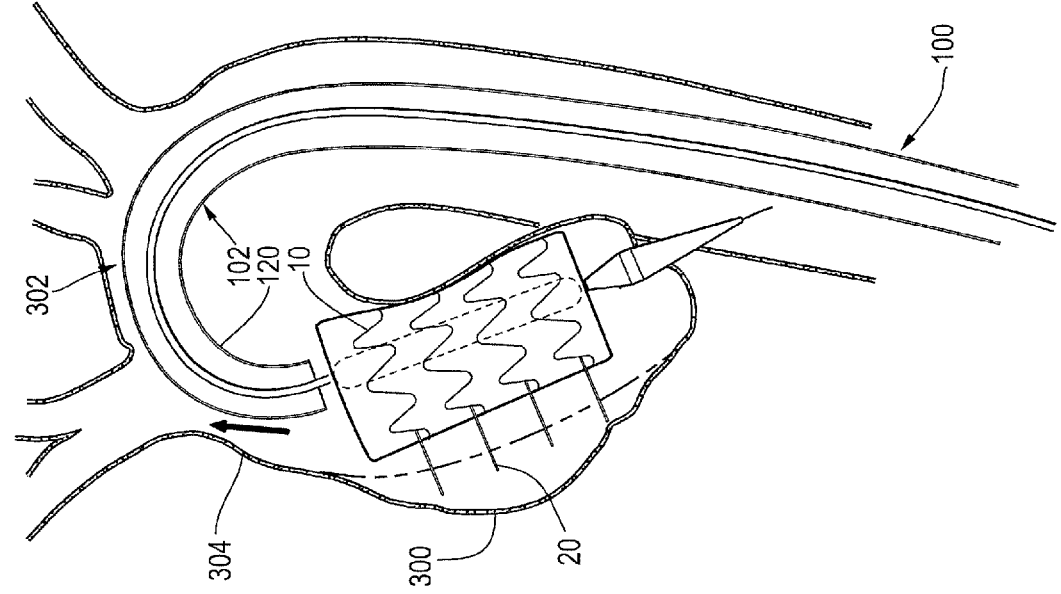
Figure 13H:
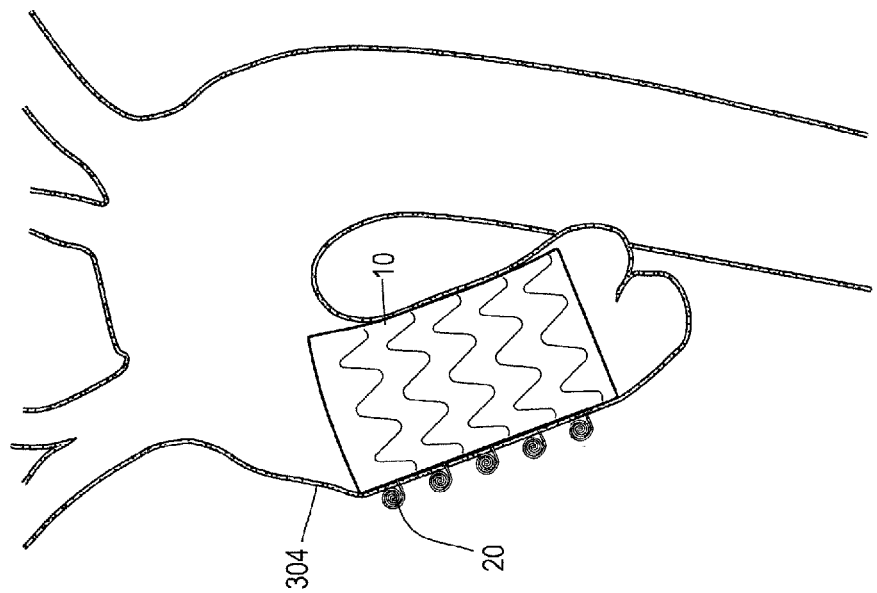
Figure 13G:
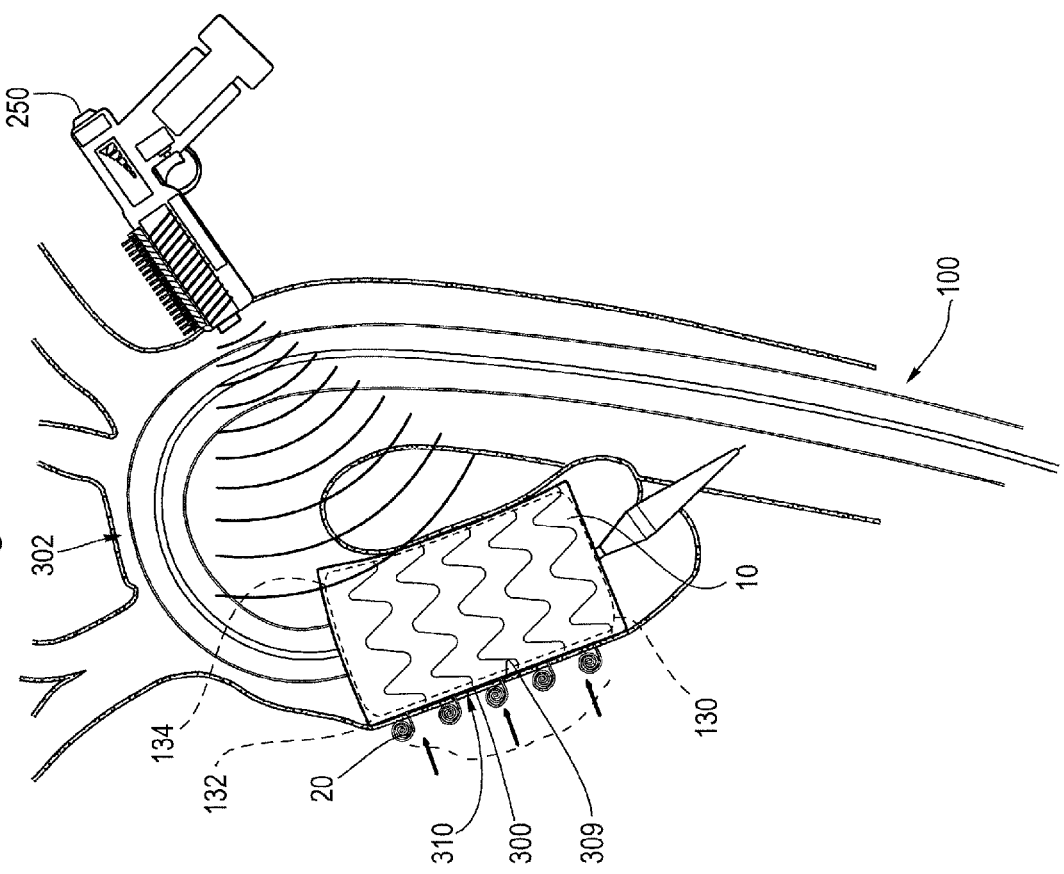

FIGS. 13A-13H illustrate a method of use of the system and for treatment of an aneurysm 300 formed in the aorta 302, such as the ascending aorta 304. The guide wire 111 may be received within a lumen of the inner cannula. The guide wire 111 may facilitate the placement of various other devices, devices, or components (for example, the balloon described below) within the vasculature of the patient. An introducer sheath may be used to guide the guide wire 111 using the femoral approach. The guide wire 111 may be moved within the body vessel beyond the treatment site. Using the system and visual techniques such as fluoroscopy, a physician may introduce the medical device in the delivery configuration within the system 100 into the femoral artery and guide the system with the medical device into position within the ascending aorta, such as, for example, along the aneurysm section or dissection section, such as shown in FIG. 13A. The medical device 10 may be positioned using the radiopaque markers. The medical device 10 may remain at least partially restrained in a radially compressed configuration, for example, by one or more diameter reducing ties or retention devices. The diameter reducing ties may be applied to the proximal and distal stents to retain the inflow and outflow ends in a reduced diameter configuration after retraction of the outer sheath, such as by tied thread and trigger wire arrangement. The stent member(s) may be released upon removal of the trigger wire to allow expansion of the medical device. The diameter reducing ties also may be configured as any other type of constraining member capable of reducing the diameter of a stent of the prosthesis.

In FIG. 13B, partial retraction of the outer sheath 120 allows movement of the anchor elements 20 from the delivery configuration to the first deployment configuration. Depending on the relative placement between the anchor elements 20 and the aortic wall, at least one of the anchor elements 20 may begin piercing the aortic aneuryzed wall 309. It is contemplated that there may not be any initial piercing at this step. FIG. 13C shows full radial expansion of the medical device 10 to its nominal expanded diameter.

A delivery system without a balloon may be removed and another balloon catheter may be positioned within the expanded medical device. Alternatively, the system 102 with the balloon(s), such as described above, may be repositioned or the position maintained within the expanded medical device 10. Inflation fluid may be introduced to the balloons 130, 132 for selectively expanding at least one of the inflatable balloons to apply targeted radial pressure within the expanded medical device 10 and potentially expand the medical device beyond its nominal expanded diameter such that the relevant anchor elements 20 pierce the aortic aneuryzed wall 309. The piercing action may allow the anchor tips to extend beyond the aortic aneuryzed wall 309 to the abluminal side 310 of the ascending aorta 304.

In FIG. 13E, the anchor elements 20 with the tips at the abluminal side 310 of the aortic aneuryzed wall are heated. In one example, the induction device 250 may be used as the inductive heating source. The heating to the required temperature facilitates movement of the anchor elements 20 from the first deployment configuration to the second deployment configuration, as shown in FIG. 13F. In the second deployed configuration, at least a portion of the anchor elements 20 have an enlarged portion configuration along the abluminal side 310 of the pierced aortic aneuryzed wall 309 such that the medical device and the pierced aortic aneuryzed wall are moved relatively closer to one another. The heating step may occur while maintaining the balloons 130, 132 in the inflated state within the medical device. The heating continues until the complete coiled or looped configuration is formed and the distance between the aortic aneuryzed wall 309 and the medical device 10 is closed. When the medical device includes a layer or coating comprising hemorrhage inhibitor, such as, for example, SIS, blood and piercings may experience healing. In FIG. 13H, the balloons are deflated, thereby allowing the medical device 10 to restore to its nominal expanded diameter, which further reduces the diameter of the ascending aorta. The system 100 and the guide wire 111 are removed from the body, and the medical device 10 remains within the body vessel.

As shown in FIGS. 13A-13H, the medical device 10 with the active anchor elements 20 may safely reshape an aneurysmal site. One such site may include the ascending aorta which has been conventionally difficult to treat due to the unique vessel geometry and lack of healthy sealing necks into which to anchor. The medical device 10 with the active anchor elements 20 may overcome any such geometry restrictions and anchoring challenges and facilitate restoring aortic diameter to a healthy aortic diameter thereby inhibiting imminent aortic rupture. The secured engagement and enhanced sealing of the vessel against the medical device may reduce the risk of type II endoleaks.

Figure 14C:
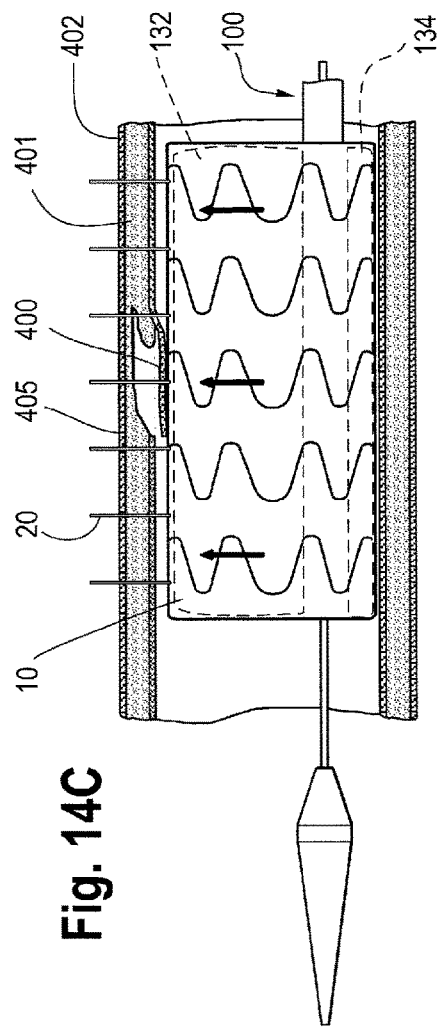

In FIGS. 14A-14E, it is contemplated that the medical device 10 with the active anchor elements 20 and/or the delivery system 100 may be beneficial for treatment of a dissection flap, such as, for example, pulling back a detached outer tissue layer of the aorta to the tunica intima or dissection flap, for example, for treatment of type A or B-dissections. FIG. 14A depicts the medical device 10 positioned at the treatment site, in this case a dissection flap 400 torn from the wall 401 of the aorta 402. The medical device 10 is loaded onto the delivery system 100 and the system 100 tracks along the guide wire 111 for positioning of the medial device 10 at the dissection flap 400. FIG. 14B depicts the proximal end of the outer sheath 120 removed from the medical device 10 to allow for expansion. During the removal, the active anchor elements may move for the delivery configuration to the first deployment configuration, as shown. The anchor elements may initiate piercing of the wall 401 and the flap 400 at this step.

Figure 14E:
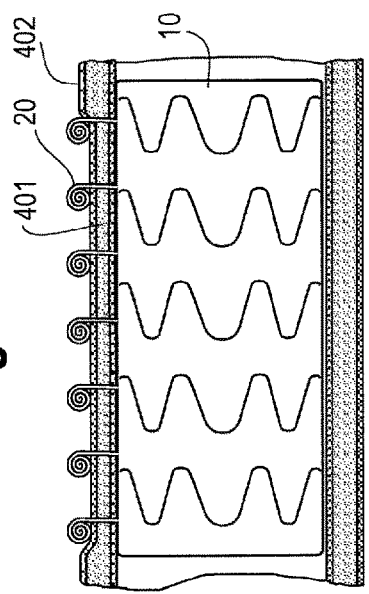
Figure 14D:
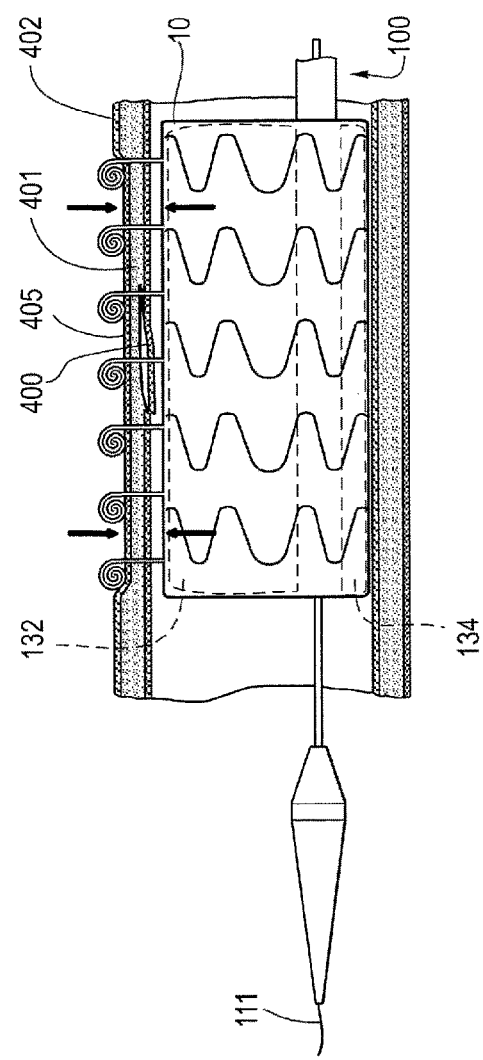

In FIG. 14C, the first and second balloons 132, 134 are expanded within the medical device to target the radial pressure of piercing toward the location of the active anchor elements 20. For example, the first balloon 132 is shown expanded larger than the second balloon 134. The piercing action may allow the anchor tips to extend beyond the wall 401 to the abluminal side 405 of the wall 401. In FIG. 14D, the anchor elements 20 with the tips at the abluminal side 405 of the wall 400 are heated. In one example, the induction device 250 may be used as the inductive heating source. The heating to the required temperature facilitates movement of the anchor elements 20 from the first deployment configuration to the second deployment configuration. In the second deployment configuration, at least a portion of the anchor elements 20 have an enlarged portion configuration along the abluminal side 405 of the pierced wall 401 such that the medical device 10 and the pierced aortic wall 401 are moved relatively closer to one another. The heating step may occur while maintaining the balloons 130, 132 in the inflated state within the medical device. The heating continues until the complete coiled or looped configuration is formed and the distance between the aortic wall 401 and the medical device 10 is closed. To this end, the dissection flap 400 is moved into engagement with the wall 401 to close off the false lumen defined between the flap and the wall and to allow for healing of the flap. When the medical device includes a layer or coating comprising hemorrhage inhibitor, such as, for example, SIS, blood and piercings may experience healing. In FIG. 14E, the balloons are deflated, thereby allowing the medical device 10 to restore to its nominal expanded diameter, which further reduces the diameter of the aorta. The system 100 and the guide wire 111 are removed from the body, and the medical device 10 remains within the body vessel.

It is understood that any of the methods of use and treatment with the medical device described herein may include a medical device without a graft covering. The medical device 10 with the active anchor elements 20 may be used to reinforce the weakened and enlarged body vessel. In some examples, after implantation of the medical device with the active anchor elements, the implanted device may also have use in providing radial scaffolding for a secondary device to attach to. The implanted device may then be used to provide suitable anchorage for secondary endografts or other devices. Other body vessel, duct or pathway diseases or reshaping are possible.

A therapeutically effective amount of a bioactive agent may be applied to the anchor elements and/or graft covering of the medical device for facilitating treatment. For example, the bioactive agent may be selected to treat indications such as atherosclerosis, renal dialysis fistulae stenosis, or vascular graft stenosis. A coating of a graft material including a bioactive agent may be useful when performing procedures such as coronary artery angioplasty, renal artery angioplasty, or carotid artery surgery. Also for example, a bioactive agent such as a growth factor may be selected to promote ingrowth of tissue from the interior wall of a body vessel. An anti-angiogenic or antineoplastic bioactive agent such as paclitaxel, sirolimus or a rapamycin analog, such as zotarolimus, everolimus, biolimus, or a metalloproteinase inhibitor such as batimastaat may be included to mitigate or prevent undesired conditions in the vessel wall, such as restenosis. Many other types of bioactive agents also may be included in the solution. Just some examples of the large range of bioactive materials which can be applied to the medical device for treating targeted diseases or issues include but are not limited to: paclitaxel, heparin, azathioprine or azathioprine sodium; basiliximab; cyclosporin or cyclosporine (cyclosporin A); daclizumab (dacliximab); glatiramer or glatiramer acetate; muromonab-CD3; mycophenolate, mycophenolate mofetil (MMF), mycophenolate morpholinoethyl or mycophenolic acid; tacrolimus (FK506), anhydrous tacrolimus or tacrolimus monohydrate; sirolimus; interferon alfa-2a, recombinant (rIFN-A or IFLrA); antilymphocyte immunoglobulin (ALG), antithymocyte immunoglobulin (ATG), antilymphocyte serum, antithymocyte serum, lymphocytic antiserum or thymitic antiserum; brequinar or brequinar sodium; cyclophosphamide, cyclophosphamide monohydrate or anhydrous cyclophosphamide; dactinomycin, actinomycin C, actinomycin D or meractinomycin; daunorubicin, daunorubicin hydrochloride, daunomycin hydrochloride or rubidomycin hydrochloride; doxorubicin, doxorubicin hydrochloride, adriamycin or adriamycin hydrochloride; fluorouracil; gusperimus or gusperimus hydrochloride; inolimomab; leflunomide; mercaptopurine, mercaptopurine monohydrate, purinethiol or anhydrous mercaptopurine; methotrexate, methotrexate sodium, methotrexate disodium, alpha-methopterin or amethopterin; mustine, mustine hydrochloride, chlormethine hydrochloride, chlorethazine hydrochloride, mechlorethamine hydrochloride or nitrogen mustard (mustine); mizoribine; vinblastine, vinblastine sulfate or vincaleukoblastine sulphate; a pharmacologically or physiologically acceptable salt of any of the foregoing; or a pharmacologically or physiologically acceptable mixture of any two or more of the foregoing. These bioactive agents have effects known in the art including as thrombolytics, vasodilators, antihypertensive agents, antimicrobials or antibiotics, antimitotics, antiproliferatives, antisecretory agents, non-steroidal anti-inflammatory drugs, immunosuppressive agents, growth factors and growth factor antagonists, antitumor and/or chemotherapeutic agents, antipolymerases, antiviral agents, photodynamic therapy agents, antibody targeted therapy agents, prodrugs, sex hormones, free radical scavengers, antioxidants, biologic agents, radiotherapeutic agents, radiopaque agents and radiolabelled agents.

To clarify the use of and to hereby provide notice to the public, the phrases "at least one of <A>, <B>, . . . and <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

I claim:

1. A medical device disposed about a longitudinal axis, comprising: a device body comprising a stent frame structure; at least one anchor element comprising a thermal activatable material, the at least one anchor element comprising a base and an anchor tip at an end opposite from the base, wherein the base is coupled to the stent frame structure; and wherein the at least one anchor element is adjustable between: a first configuration, where the at least one anchor element is disposed about an anchor axis substantially perpendicular to the longitudinal axis and the anchor tip is configured to pierce completely through a body tissue wall; and in response to a temperature rise in the at least one anchor element, a second configuration, wherein, a portion of the at least one anchor element is configured to press against an exterior of a pierced body tissue wall to press the pierced body tissue wall closer to the device body, and the at least one anchor element within the body tissue wall is configured to maintain alignment substantially with the anchor axis to inhibit tearing of the pierced body tissue wall by the at least one anchor element.

2. The medical device of claim 1, wherein in the first configuration the at least one anchor element includes an elongated shape and the anchor tip is positioned extending outwardly from the device body.

3. The medical device of claim 2, wherein the at least one anchor element includes a wire member having a first profile perpendicular to the anchor axis in the first configuration, and in the second configuration the wire member is shaped to define a second profile perpendicular to the anchor axis that is greater than the first profile.

4. The medical device of claim 1, wherein the anchor tip is positioned relatively closer to the device body in the second configuration than in the first configuration.

5. The medical device of claim 4, wherein an end of the at least one anchor element spaced from the base and outside of the pierced body tissue wall is shaped having a coiled or looped configuration in the second configuration.

6. The medical device of claim 1, wherein the at least one anchor element, in response to the temperature rise, is pivotable about the base within 15 degrees of the anchor axis.

7. The medical device of claim 1, wherein the at least one anchor element comprises a plurality of anchor elements disposed along a discrete region of the device body.

8. The medical device of claim 1, wherein the at least one anchor element comprises a plurality of anchor elements disposed circumferentially along the device body.

9. The medical device of claim 1, wherein the thermal activatable material includes a shape memory material.

10. The medical device of claim 1, wherein the stent frame structure comprises an expandable stent support ring structure, and wherein the at least one anchor element is securely fixed to the expandable stent support ring structure.

11. A delivery system for deployment of a prosthesis within a body vessel, comprising: an outer sheath coaxially disposed over an inner cannula, the outer sheath and the inner cannula defining a retention region; and the prosthesis including a prosthesis body resiliently movable between a radially compressed configuration and a radially expanded configuration, and a plurality of thermal activatable anchor elements, each of the plurality of thermal activatable anchor elements having a base and an anchor tip at an end opposite from the base, wherein the base is coupled along the prosthesis body; the plurality of thermal activatable anchor elements including: a delivery configuration when the prosthesis is in the radially compressed configuration, wherein the prosthesis is disposed along the retention region and retained in the radially compressed configuration by the outer sheath; a first deployed configuration wherein, with retraction of the outer sheath, the prosthesis is movable to the radially expanded configuration and the plurality of thermal activatable anchor elements are resiliently movable from the delivery configuration to pierce completely through a body tissue wall of the body vessel, and a second deployed configuration wherein, in response to an increase in temperature of the plurality of thermal activatable anchor elements in the first deployed configuration, the plurality of thermal activatable anchor elements are movable to press portions of the plurality of thermal activatable anchor elements extending through a pierced body vessel wall against an exterior of the body vessel to bring the prosthesis body and the pierced body tissue wall relatively closer to one another.

12. The delivery system of claim 11, further comprising at least one inflatable balloon at a proximal end of the inner cannula, wherein the at least one inflatable balloon is positionable within the prosthesis in the radially expanded configuration, wherein in response to expansion of the at least one inflatable balloon, a piercing pressure of the plurality of thermal activatable anchor elements in the first deployed configuration is increasable.

13. The delivery system of claim 12, wherein the at least one inflatable balloon includes a first inflatable balloon and a second inflatable balloon disposed in a longitudinal side-by-side relationship at the proximal end of the inner cannula, the system further comprising an inflation reservoir divided into a first chamber and a second chamber by a piston, the first chamber in fluid communication with the first inflatable balloon and the second chamber in fluid communication with the second inflatable balloon, wherein movement of the piston within the inflation reservoir selectively increases or decreases fluid volumes of the respective first and second chambers such that a cross-sectional area of expansion of the corresponding first and second inflatable balloons are selectively and independently increased or decreased.

14. The delivery system of claim 11, wherein each of the plurality of thermal activatable anchor elements in the first deployed configuration is disposed about an anchor axis, and wherein, in response to said temperature rise and movement to the second deployed configuration, each of the plurality of thermal activatable anchor elements maintains alignment substantially with the anchor axis to inhibit tearing of the pierced body tissue wall.

15. A medical device disposed about a longitudinal axis, comprising: a device body comprising a stent frame structure; at least one anchor element comprising a thermal activatable material, the at least one anchor element comprising a base and an anchor tip at an end opposite from the base, wherein the base is coupled to the stent frame structure; and wherein the at least one anchor element is adjustable between: a first configuration, where the at least one anchor element is disposed about an anchor axis substantially perpendicular to the longitudinal axis and the anchor tip is configured to pierce completely through a body tissue wall; and in response to a temperature rise in the at least one anchor element, a second configuration where the at least one anchor element is configured to: at a first portion of the at least one anchor element adjacent the base and extending through the body tissue wall, maintain alignment substantially with the anchor axis to inhibit tearing of a pierced body tissue wall by the at least one anchor element; and at a second portion of the at least one anchor element extending outside the body tissue wall and adjacent the anchor tip, press against an exterior of the body tissue wall to bring the prosthesis body and the pierced body tissue wall relatively closer to one another.

16. The medical device of claim 15, wherein the anchor tip is positioned relatively closer to the device body in the second configuration than in the first configuration.

17. The medical device of claim 15, wherein the second portion of the at least one anchor element is shaped having a coiled or looped configuration in the second configuration.

18. The medical device of claim 15, wherein the at least one anchor element, in response to the temperature rise, is pivotable about the base within 15 degrees of the anchor axis.

* * * * *